(12) United States Patent
Li et al.

(10) Patent No.: US 8,268,884 B2
(45) Date of Patent: Sep. 18, 2012

(54) DERIVATIVES OF SUBSTITUTED TARTARIC ACID AND USAGE FOR PREPARING BETA-SECRETASE INHIBITORS

(75) Inventors: Song Li, Beijing (CN); Guochao Liao, Beijing (CN); Junhai Xiao, Beijing (CN); Aihua Nie, Beijing (CN); Lili Wang, Beijing (CN); Wu Zhong, Beijing (CN); Zhibing Zheng, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 371 days.

(21) Appl. No.: 12/521,425

(22) PCT Filed: Feb. 5, 2007

(86) PCT No.: PCT/CN2007/000389
§ 371 (c)(1),
(2), (4) Date: Nov. 13, 2009

(87) PCT Pub. No.: WO2008/080268
PCT Pub. Date: Jul. 10, 2008

(65) Prior Publication Data
US 2010/0331345 A1 Dec. 30, 2010

(30) Foreign Application Priority Data
Dec. 29, 2006 (CN) .......................... 2006 1 0156136

(51) Int. Cl.
*A61K 31/225* (2006.01)
*A61K 31/235* (2006.01)
*C07C 229/00* (2006.01)

(52) U.S. Cl. ........... 514/533; 514/547; 560/40; 560/169
(58) Field of Classification Search .................. 514/533, 514/547; 560/40, 169
See application file for complete search history.

(56) References Cited

U.S. PATENT DOCUMENTS
3,527,735 A 9/1970 Horvath et al.
2004/0171881 A1* 9/2004 John et al. ...................... 564/163
2006/0178366 A1 8/2006 Siddiqui et al.

FOREIGN PATENT DOCUMENTS
CN 1660826 A 8/2005
WO WO 98/16502 * 4/1998
WO WO 03/040096 A2 5/2003
WO WO 2004/022523 A2 3/2004

OTHER PUBLICATIONS

Intelihealth, "Alzheimer's disease," online, accessed Jun. 30, 2008, http://www. intelihealth.com /IH/intlh/ WSIHW000/ 8303/9117/ 195703.html?d= dmtHealthAZ.*
Intelihealth, "Amyloidosis," online, accessed Mar. 2009, http://www. intelihealth.com/ IH/ihtlH/ WSIHW000/ 9339/9444. html#treat.*
Intelihealth, "Down syndrome," online, accessed Dec. 2011, http://www.inteli health.com/IH/ihtl H?t=9844& p=~br,IHW|~st,24479|~r, WSIHW000|~b,|.*
International Search Report of PCT/ CN2007/000389.
Casale, I. L. "Tartaric Amides and Imides" Gazzetta Chimica Italiana (1917), 47(I), 272-85.
Wilkins, S. M. et al. "Enantiomer Separations by Supercritical Fluid Chromatography on a Chiral Stationary Phase Physically Anchored to Porous Graphitic Carbon" Journal of Chromatography, A (1995), 697, 587-90.
"JP2002-326995 Abstract," *Database WPI Week* 200315, Thomson Scientific, London, GB, 2002, XP-002667533.
"JP3266819 Abstract," *Database WPI Week* 199203, Thomson Scientific, London, GB, 1991, XP-002667534.
Massicot, F.; Plantier-Royon, R.; Portella, C.; Saleur, D.; Sudha, A.V.R.L. "Solvent-Free Synthesis of Tartramides Under Microwave Activation," *Synthesis*, 2001 16, 2441-2444.
Supplementary Partial European Search Report dated Jan. 31, 2012 for co-pending European Application No. 077022762.

* cited by examiner

*Primary Examiner* — Paul Zarek
(74) *Attorney, Agent, or Firm* — Brinks Hofer Gilson & Lione

(57) ABSTRACT

The present invention relates to compounds represented by formula (I), or isomers, prodrugs, pharmaceutically acceptable salts, solvates or hydrates thereof:

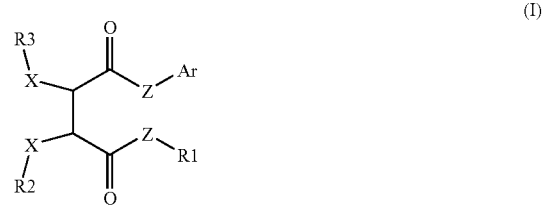

(I)

in which each substituent of formula (I) is as defined in the specification. The present invention also relates to preparation methods of compounds represented by formula (I), a pharmaceutical composition comprising compounds represented by formula (I) and usage of compounds represented by formula (I) for treating chronic neurodegenerative diseases such as Alzheimer's disease and other diseases induced by aggregation or deposition of β-amyloid peptide.

5 Claims, No Drawings

DERIVATIVES OF SUBSTITUTED TARTARIC ACID AND USAGE FOR PREPARING BETA-SECRETASE INHIBITORS

TECHNICAL FIELD

The present invention relates to derivatives of substituted tartaric acid, processes for preparing them, a pharmaceutical composition comprising them, and usage thereof as β-secretase inhibitors for preparing a medicament for treating and/or preventing chronic neurodegenerative diseases such as Alzheimer's disease and other diseases induced by aggregation or deposition of β-amyloid peptide.

BACKGROUND ART

Alzheimer's disease is a familiar chronic neurodegenerative disease, which is clinically expressed as progressive hypomnesia and cognitive disorder, and final loss of self-care ability, and is pathologically characterized by the occurrence of neurofibrillary tangle inside nerve cells and extracellular senile plaque. The principal components of senile plaque include a series of β-amyloid peptides, Aβ, having various lengths.

Aβ is a polypeptide containing 39 to 43 amino acids, and is derived from β-amyloid precursor protein, β-APP. There are two routes for cleavage of β-APP in vivo: non-amyloid route and amyloid route. Non-amyloid route refers to cleavage of β-APP with α-secretase, γ-secretase, without resulting in Aβ. Amyloid route refers to cleavage of β-APP at N-terminal with β-secretase, to form β-CTF (C-terminal fragments) including entire Aβ sequence, followed by cleavage of β-CTF with γ-secretase to result in Aβ.

β-secretase belongs to Asp protease, and is also called as BACE1, Asp2 or Memapsin-2 (Sinha S, Anderson J P, Barbour R, et al: *Nature*, 1999, 402(6761): 537-540). Due to disequilibrium of production and metabolism, dissociation and aggregation of Aβ, an abnormal amount of Aβ gradually aggregates to form senile plaque, which subsequently leads to pathological changes including neurofibrillary tangle, microgliocyte inflammation, neuron apoptosis, neurotransmitter deficiency and etc., and finally results in senile dementia. β-Secretase is a rate-limiting enzyme for producing Aβ. Thus, it is possible to prevent or treat Alzheimer's disease by inhibiting the activity of β-secretase to decrease or block the production of Aβ, to thereby reduce the content of Aβ, and prevent aggregation of Aβ in brain which leads to the formation of senile plaque (Hardy J, Dennis D J. *Science*, 2002, 297:353-356). Meanwhile, it is also possible to prevent or treat other diseases such as amyloid degenerative angiopathy, Kuru's disease and Down's syndrome induced by aggregation or deposition of Aβ.

BACE1 gene knock-out mouse had no production of Aβ in brain, and lived substantially normally, which further demonstrated that it was possible to prevent or treat diseases induced by aggregation or deposition of Aβ, in particular neurodegenerative diseases such as Alzheimer's disease, by blocking the production of Aβ, while, as presumed, would not result in much great side effect (Roberds S L, Anderson J, Basi G, et al: *Hum Mol Genet*, 2001, 10(12): 1317-1324).

CONTENTS OF THE INVENTION

The objection of the invention is to search for and develop β-secretase inhibitors, which are used for treating or preventing relevant neurodegenerative diseases such as Alzheimer's disease and the like and other diseases such as amyloid degenerative angiopathy, Kuru's disease and Down's syndrome induced by aggregation or deposition of β-amyloid peptide, by inhibiting the activity of β-secretase to decrease or block the metabolism of β-amyloid precursor protein with β-secretase to result in β-amyloid peptide, to thereby reduce the content of β-amyloid peptide, and prevent aggregation of β-amyloid peptide in brain which leads to the formation of senile plaque.

By study, the present inventors discover that the following compound of formula I has the activity of inhibiting β-secretase, and is capable of decreasing the metabolism of β-amyloid precursor protein with β-secretase to result in β-amyloid peptide, to thereby reduce the content of β-amyloid peptide and prevent aggregation or deposition of β-amyloid peptide in vivo. Thus, β-secretase inhibitors can be used for treating or preventing relevant neurodegenerative diseases such as Alzheimer's disease and the like and other diseases such as amyloid degenerative angiopathy, Kuru's disease and Down's syndrome induced by aggregation or deposition of β-amyloid peptide.

In one aspect, the present invention relates to a compound of formula I, or all possible isomers, prodrugs, pharmaceutically acceptable salts, solvates or hydrates thereof:

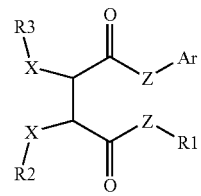

wherein:

X is O, S;

Z is $CH_2$, O, S, NH;

R1 is $C_1$-$C_{22}$ linear or branched alkyl, $C_2$-$C_{22}$ linear or branched alkenyl, $C_3$-$C_8$ cycloalkyl, $C_5$-$C_7$ cycloalkenyl or $Ar_1$, wherein the alkyl or alkenyl radical is unsubstituted or substituted by one or more of the following groups: halogen, nitro, hydroxy, amino, cyano, carboxy, $Ar_2$, $C_3$-$C_8$ cycloalkyl, $C_5$-$C_7$ cycloalkenyl, O—($C_1$-$C_4$)-alkyl or $Ar_2$, CO—($C_1$-$C_4$)-alkyl or $Ar_2$, SO—($C_1$-$C_4$)-alkyl or $Ar_2$, N—[($C_1$-$C_6$)-alkyl]$_2$, NH—($C_1$-$C_6$)-alkyl or $Ar_2$, N—[($C_1$-$C_6$)-alkyl $Ar_2$], COO—($C_1$-$C_6$)-alkyl or $Ar_2$, CONH—($C_1$-$C_6$)-alkyl or $Ar_2$, SONH—($C_1$-$C_6$)-alkyl or $Ar_2$; in addition, the C atoms in the alkyl and alkenyl radicals are optionally spaced by —O—, —S—, —NH—, —N═, —S—, —$Ar_2$—, —SO—, —CO—, —COO—, —CONH—, —SOO—, —SONH—, —N[($C_1$-$C_6$)-alkyl or $Ar_2$]—;

R2 and R3, which are the same or different, are independently selected from the group consisting of hydrogen, hydroxy, $C_1$-$C_{12}$ linear or branched alkyl, $C_2$-$C_{12}$ linear or branched alkenyl, $C_3$-$C_7$ cycloalkyl, $Ar_1$, ($C_1$-$C_6$)—$Ar_1$, —CO—($C_1$-$C_6$)-alkyl or alkenyl or $Ar_1$, —SO—($C_1$-$C_6$)-alkyl or alkenyl or $Ar_1$, SOO—($C_1$-$C_6$)-alkyl or alkenyl;

Ar, $Ar_1$ and $Ar_2$ are independently selected from the group consisting of aromatic carbocycles or heterocycles, wherein each of the cycles consists of 5 to 7 members, and the number of the cycles is monocycle, bicycle or tricycle; the heterocycle includes 1 to 6 heteroatoms selected from the group consisting of O, S, N; the aromatic carbocycles or heterocycles are unsubstituted, or substituted by 1 to 4 groups selected from the group consisting of halogen, nitro, hydroxy, amino, cyano, carboxy, methylol, trifluoromethyl, phenoxy, benzyloxy, anilino, benzylamino, $C_1$-$C_7$ linear or branched alkyl, $C_2$-$C_7$ linear or branched alkenyl, $C_3$-$C_7$ cycloalkyl, $C_5$-$C_7$ cycloalkenyl, —O—($C_1$-$C_6$)-alkyl or alkenyl, —CO—($C_1$-$C_6$)-alkyl or alkenyl, —SO—($C_1$-$C_6$)-alkyl or alkenyl, —NH—($C_1$-$C_6$)-alkyl or alkenyl, —N—[($C_1$-$C_6$)-alkyl or alkenyl]$_2$, —COO—($C_1$-$C_6$)-alkyl or alkenyl, —CONH—($C_1$-$C_6$)-alkyl or alkenyl, —SONH—($C_1$-$C_6$)-alkyl or alkenyl, —CON[($C_1$-$C_6$)-alkyl or alkenyl]$_2$, —SON[($C_1$-$C_6$)-alkyl or alkenyl]$_2$;

the substituent R2X— and the substituent R3X— have the same or different configuration, being R-configuration or S-configuration.

In one preferred embodiment, the present invention relates to a compound of formula Ia:

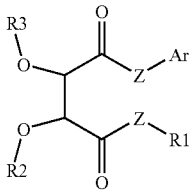

Ia wherein:

Z is $CH_2$, O, S, NH;

R1 is $C_1$-$C_{22}$ linear or branched alkyl, $C_2$-$C_{22}$ linear or branched alkenyl, $C_3$-$C_8$ cycloalkyl, $C_5$-$C_7$ cycloalkenyl or $Ar_1$, wherein the alkyl or alkenyl radical is unsubstituted or substituted by one or more of the following groups: halogen, nitro, hydroxy, amino, cyano, carboxy, $Ar_2$, $C_3$-$C_8$ cycloalkyl, $C_5$-$C_7$ cycloalkenyl, O—($C_1$-$C_4$)-alkyl or $Ar_2$, CO—($C_1$-$C_4$)-alkyl or $Ar_2$, SO—($C_1$-$C_4$)-alkyl or $Ar_2$, N—[($C_1$-$C_6$)-alkyl]$_2$, NH—($C_1$-$C_6$)-alkyl or $Ar_2$, N—[($C_1$-$C_6$)-alkyl $Ar_2$], COO—($C_1$-$C_6$)-alkyl or $Ar_2$, CONH—($C_1$-$C_6$)-alkyl or $Ar_2$, SONH—($C_1$-$C_6$)-alkyl or $Ar_2$; in addition, the C atoms in the alkyl and alkenyl radicals are optionally spaced by —O—, —S—, —NH—, —N=, —S—, —$Ar_2$—, —SO—, —CO—, —COO—, —CONH—, —SOO—, —SONH—, —N[($C_1$-$C_6$)-alkyl or $Ar_2$]—;

R2 and R3, which are the same or different, are independently selected from the group consisting of hydrogen, hydroxy, $C_1$-$C_{12}$ linear or branched alkyl, $C_2$-$C_{12}$ linear or branched alkenyl, $C_3$-$C_7$ cycloalkyl, $Ar_1$, ($C_1$-$C_6$)—$Ar_1$, —CO—($C_1$-$C_6$)-alkyl or alkenyl or $Ar_1$, —SO—($C_1$-$C_6$)-alkyl or alkenyl or $Ar_1$, SOO—($C_1$-$C_6$)-alkyl or alkenyl;

Ar, $Ar_1$ and $Ar_2$ are independently selected from the group consisting of aromatic carbocycles or heterocycles, wherein each of the cycles consists of 5 to 7 members, and the number of the cycles is monocycle, bicycle or tricycle; the heterocycle includes 1 to 6 heteroatoms selected from the group consisting of O, S, N; the aromatic carbocycles or heterocycles are unsubstituted, or substituted by 1 to 4 groups selected from the group consisting of halogen, nitro, hydroxy, amino, cyano, carboxy, methylol, trifluoromethyl, phenoxy, benzyloxy, anilino, benzylamino, $C_1$-$C_7$ linear or branched alkyl, $C_2$-$C_7$ linear or branched alkenyl, $C_3$-$C_7$ cycloalkyl, $C_5$-$C_7$ cycloalkenyl, —O—($C_1$-$C_6$)-alkyl or alkenyl, —CO—($C_1$-$C_6$)-alkyl or alkenyl, —SO—($C_1$-$C_6$)-alkyl or alkenyl, —NH—($C_1$-$C_6$)-alkyl or alkenyl, —N—[($C_1$-$C_6$)-alkyl or alkenyl]$_2$, —COO—($C_1$-$C_6$)-alkyl or alkenyl, —CONH—($C_1$-$C_6$)-alkyl or alkenyl, —SONH—($C_1$-$C_6$)-alkyl or alkenyl, —CON[($C_1$-$C_6$)-alkyl or alkenyl]$_2$, —SON[($C_1$-$C_6$)-alkyl or alkenyl]$_2$;

the substituent R2X— and the substituent R3X— have the same or different configuration, being R-configuration or S-configuration.

In one further preferred embodiment, the present invention relates to a compound of formula Ib:

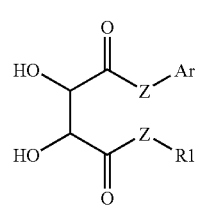

Ib wherein:

Z is $CH_2$, O, S, NH;

R1 is $C_1$-$C_{22}$ linear or branched alkyl, $C_2$-$C_{22}$ linear or branched alkenyl, $C_3$-$C_8$ cycloalkyl, $C_5$-$C_7$ cycloalkenyl or $Ar_1$, wherein the alkyl or alkenyl radical is unsubstituted or substituted by one or more of the following groups: halogen, nitro, hydroxy, amino, cyano, carboxy, $Ar_2$, $C_3$-$C_8$ cycloalkyl, $C_5$-$C_7$ cycloalkenyl, O—($C_1$-$C_4$)-alkyl or $Ar_2$, CO—($C_1$-$C_4$)-alkyl or $Ar_2$, SO—($C_1$-$C_4$)-alkyl or $Ar_2$, N—[($C_1$-$C_6$)-alkyl]$_2$, NH—($C_1$-$C_6$)-alkyl or $Ar_2$, N—[($C_1$-$C_6$)-alkyl $Ar_2$], COO—($C_1$-$C_6$)-alkyl or $Ar_2$, CONH—($C_1$-$C_6$)-alkyl or $Ar_2$, SONH—($C_1$-$C_6$)-alkyl or $Ar_2$; in addition, the C atoms in the alkyl and alkenyl radicals are optionally spaced by —O—, —S—, —NH—, —N=, —S—, —$Ar_2$—, —SO—, —CO—, —COO—, —CONH—, —SOO—, —SONH—, —N[($C_1$-$C_6$)-alkyl or $Ar_2$]—;

Ar, $Ar_1$ and $Ar_2$ are independently selected from the group consisting of aromatic carbocycles or heterocycles, wherein each of the cycles consists of 5 to 7 members, and the number of the cycles is monocycle, bicycle or tricycle; the heterocycle includes 1 to 6 heteroatoms selected from the group consisting of O, S, N; the aromatic carbocycles or heterocycles are unsubstituted, or substituted by 1 to 4 groups selected from the group consisting of halogen, nitro, hydroxy, amino, cyano, carboxy, methylol, trifluoromethyl, phenoxy, benzyloxy, anilino, benzylamino, $C_1$-$C_7$ linear or branched alkyl, $C_2$-$C_7$ linear or branched alkenyl, $C_3$-$C_7$ cycloalkyl, $C_5$-$C_7$ cycloalkenyl, —O—($C_1$-$C_6$)-alkyl or alkenyl, —CO—($C_1$-$C_6$)-alkyl or alkenyl, —SO—($C_1$-$C_6$)-alkyl or alkenyl, —NH—($C_1$-$C_6$)-alkyl or alkenyl, —N—[($C_1$-$C_6$)-alkyl or alkenyl]$_2$, —COO—($C_1$-$C_6$)-alkyl or alkenyl, —CONH—($C_1$-$C_6$)-alkyl or alkenyl, —SONH—($C_1$-$C_6$)-alkyl or alkenyl, —CON[($C_1$-$C_6$)-alkyl or alkenyl]$_2$, —SON[($C_1$-$C_6$)-alkyl or alkenyl]$_2$;

the two hydroxy radicals have the same or different configuration, being R-configuration or S-configuration.

As for R1 in the above compound of formula I, Ia or Ib, its definition "$C_1$-$C_{22}$ linear or branched alkyl" is more preferably $C_1$-$C_6$ linear or branched alkyl, and its definition "$C_2$-$C_{22}$ linear or branched alkenyl" is more preferably $C_2$-$C_6$ linear or branched alkenyl.

Preferably, the following compounds of formula Ia are selected:

(1) Methyl L-(2R,3R)-2-[2,3-diacetoxy-3-(naphthalen-2-ylcarbamoyl)-propionylamino]-3-phenyl-propionate;

(2) Methyl L-(2R,3R)-4-{[2,3-diacetoxy-3-(4-phenoxy-phenylcarbamoyl)-propionylamino]methyl}-benzoate;

(3) Methyl L-(2R,3R)-4-[2,3-diacetoxy-3-(4-phenoxy-phenylcarbamoyl)-propionylamino]-butyrate;

(4) Methyl L-(2R,3R)-4-{[3-(3-di-n-propylaminoformyl-phenylcarbamoyl)-2,3-diacetoxy-propionylamino]methyl}-benzoate;
(5) Dimethyl L-(2R,3R)-5-[2,3-diacetoxy-3-(1-methoxycarbonyl-2-phenyl-ethylcarbamoyl)-propionylamino]-isophthalate;
(6) Dimethyl L-(2R,3R)-5-[2,3-diacetoxy-3-(4-methoxycarbonyl-benzylcarbamoyl)-propionylamino]-isophthalate;
(7) L-(2R,3R)—N-benzyl-2,3-diacetoxy-3-(4-benzyl-piperazin-1-yl-formyl)-propionamide;

or their all possible isomers, prodrugs, pharmaceutically acceptable salts, solvates or hydrates.

More preferably, the following compounds of formula Ib are selected:
(8) Methyl L-(2R,3R)-2-(3-benzylcarbamoyl-2,3-dihydroxy-propionylamino)-3-phenyl-propionate;
(9) Methyl L-(2R,3R)-4-[(3-benzylcarbamoyl-2,3-dihydroxy-propionylamino) methyl]-benzoate;
(10) L-(2R,3R)-2-(3-benzylcarbamoyl-2,3-dihydroxy-propionylamino)-3-phenyl-propionic acid;
(11) Methyl L-(2R,3R)-4-(3-benzylcarbamoyl-2,3-dihydroxy-propionylaminomethyl)-cyclohexanecarboxylate;
(12) L-(2R,3R)-4-[(3-benzylcarbamoyl-2,3-dihydroxy-propionylamino)methyl]-benzoic acid;
(13) Methyl L-(2R,3R)-4-(3-benzylcarbamoyl-2,3-dihydroxy-propionylamino)-butyrate;
(14) L-(2R,3R)-4-(3-benzylcarbamoyl-2,3-dihydroxy-propionylamino)-butyric acid;
(15) L-(2R,3R)-4-[(3-benzylcarbamoyl-2,3-dihydroxy-propionylamino)methyl]-cyclohexanecarboxylic acid;
(16) Dimethyl L-(2R,3R)-5-(3-benzylcarbamoyl-2,3-dihydroxy-propionylamino)-isophthalate;
(17) Methyl L-(2R,3R)-4-{[2,3-dihydroxy-3-(naphthalen-2-ylcarbamoyl)-propionylamino]methyl}-benzoate;
(18) Methyl L-(2R,3R)-4-{[2,3-dihydroxy-3-(naphthalen-2-ylcarbamoyl)-propionylamino]methyl}-cyclohexanecarboxylate;
(19) Methyl L-(2R,3R)-2-[2,3-dihydroxy-3-(naphthalen-2-ylcarbamoyl)-propionylamino]-3-phenyl-propionate;
(20) Ethyl L-(2R,3R)-2-[2,3-dihydroxy-3-(4-phenoxy-phenylcarbamoyl)-propionylamino]-3-phenyl-propionate;
(21) Methyl L-(2R,3R)-4-{[2,3-dihydroxy-3-(4-phenoxy-phenylcarbamoyl)-propionylamino]methyl}-benzoate;
(22) Methyl L-(2R,3R)-4-[2,3-dihydroxy-3-(4-phenoxy-phenylcarbamoyl)-propionylamino]-butyrate;
(23) Methyl L-(2R,3R)-4-[2,3-dihydroxy-3-(naphthalen-2-ylcarbamoyl)-propionylamino]-butyrate;
(24) Ethyl L-(2R,3R)-2-[3-(3-di-n-propylaminoformyl-phenylcarbamoyl)-2,3-dihydroxy-propionylamino]-3-phenyl-propionate;
(25) Benzyl L-(2R,3R)-4-(3-benzylcarbamoyl-2,3-dihydroxy-propionylamino)-butyrate;
(26) Ethyl L-(2R,3R)-4-[2,3-dihydroxy-3-(4-phenoxy-phenylcarbamoyl)-propionylamino]-cyclohexanecarboxylate;
(27) Dimethyl L-(2R,3R)-5-[2,3-dihydroxy-3-(1-methoxycarbonyl-2-phenyl-ethylcarbamoyl)-propionylamino]-isophthalate;
(28) Methyl L-(2R,3R)-4-{[3-(3-di-n-propylaminoformyl-phenylcarbamoyl)-2,3-dihydroxy-propionylamino]methyl}benzoate;
(29) L-(2R,3R)-4-[4-(3-chlorophenyl)-piperazin-1-yl]-2,3-dihydroxy-N-naphthalen-2-yl-4-oxo-butyramide;
(30) L-(2R,3R)-3-{4-[4-(3-chlorophenyl)-piperazin-1-yl]-2,3-dihydroxy-4-oxy-butyrylamino}-N,N-di-n-propyl-benzamide;
(31) Dimethyl L-(2R,3R)-5-[2,3-dihydroxy-3-(4-methoxycarbonyl-benzylcarbamoyl)-propionylamino]-isophthalate;

or their all possible isomers, prodrugs, pharmaceutically acceptable salts, solvates or hydrates.

The present invention further relates to suitable pharmaceutically acceptable salts, solvates or hydrates of the compound of formula I, wherein the pharmaceutically acceptable salts include, but not limited to, salts formed by the compound of formula I with various inorganic acids such as hydrochloric acid, sulfuric acid, phosphoric acid, phosphorous acid, hydrobromic acid and nitric acid, and salts formed with various organic acids such as maleic acid, malic acid, fumaric acid, succinic acid, tartaric acid, citric acid, acetic acid, lactic acid, methanesulfonic acid, toluene-p-sulfonic acid, palmic acid and etc. Some compounds of the invention may be crystallized or recrystallized with water or various organic solvents, and in this case, various solvates may be formed. The present invention involves those stoichiometric solvates, including hydrates, as well as compounds with variable amount of water formed by lyophylization.

The present invention further relates to various isomers of the compound of formula I. A part of the compounds of the invention may exist in the forms of optical isomers or tautomers, and their all possible forms, in particular the forms of pure isomers, are in the scope of the invention. Different forms of isomers may be separated or resolved from other forms of isomers by various conventional means, or certain isomers may be obtained by various conventional synthetic processes or stereospecific or asymmetric synthetic processes. Since the compounds of formula I are for officinal use, it may be understood that they had better to be provided in pure form, for example, with a purity of at least 60%, more suitably 75%, more preferably 85%, most preferably at least 98% (% refers to weight percentage).

In another aspect, the present invention relates to processes for preparing a compound of formula I, or pharmaceutically acceptable salts, solvates or hydrates thereof. In particular, the present invention provides processes for preparing a compound of formula I, or pharmaceutically acceptable salts, solvates or hydrates thereof, which are respectively described below in terms of sub-class structures of the compounds.

The process for preparing the compound of formula Ia wherein R2 and R3 both are —CO—CH$_3$, and R1, Ar and Z are as defined above, is described as follows:

(i) under the catalysis of an acid such as sulfuric acid, compound 1 (L- or D-tartaric acid) and a lower fatty acid anhydride such as acetic anhydride are reacted by reflux, to obtain compound 2;

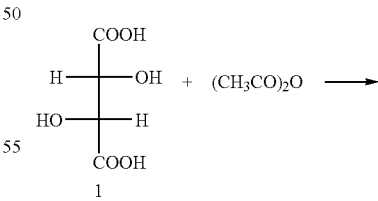

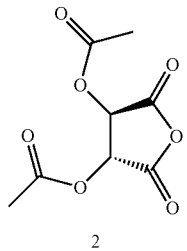

(ii) compound 2 is dissolved in a suitable solvent such as THF, dichloromethane or N,N-dimethylformamide, and acylated with equimolar of $ArNH_2$, to obtain compound 3, wherein Ar is as defined above;

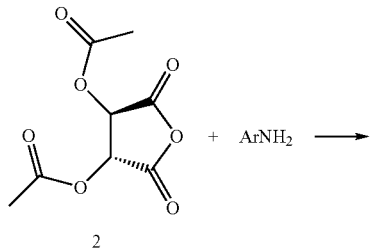

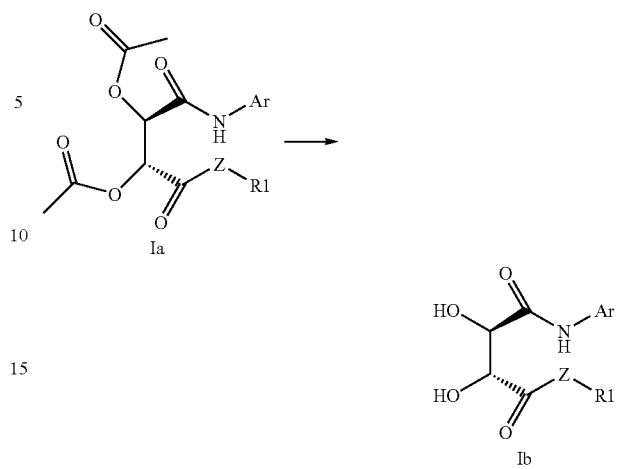

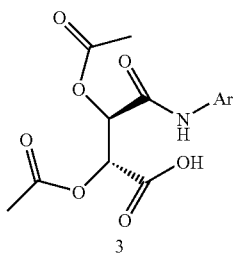

(iii) compound 3 is dissolved in a suitable solvent such as THF, dichloromethane or N,N-dimethylformamide, and, under the catalysis of a suitable amount of dicyclohexylcarbodiimide, camphorsulfonic acid and 4-dimethylaminopyridine, is acylated or esterified with R1ZH (alcohol or amine), wherein R1 and Z are as defined above, to obtain a specific compound of formula Ia of the invention;

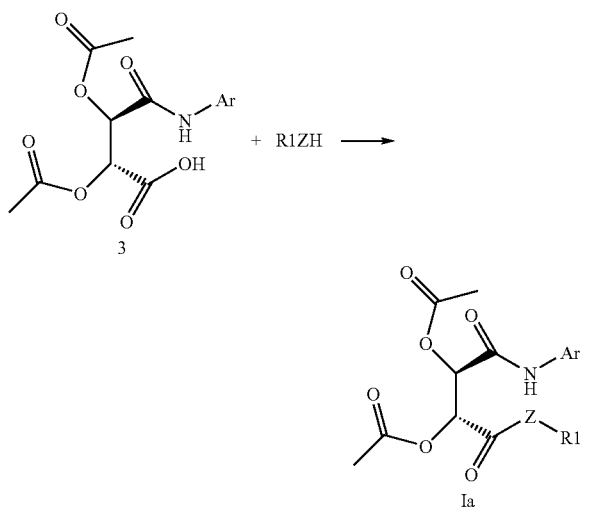

(iv) compound 1a is dissolved in a suitable solvent such as THF, methanol, ethanol, aminolyzed with a concentrated ammonia water or ammonia, hydrolyzed with sodium hydroxide, potassium hydroxide or potassium carbonate, and transesterified with sodium methoxide or sodium ethoxide, to obtain a specific compound of formula Ib of the invention.

The process for preparing the compound of formula Ib, wherein R1, Ar and Z are as defined above, is described as follows:

(i) under the catalysis of an acid such as sulfuric acid, a strong acid type ion exchange resin, compound 1 (L- or D-tartaric acid) is reacted by reflux with a fatty alcohol ROH wherein R is $C_1$-$C_4$ alkyl, such as methanol or ethanol, to obtain compound 2;

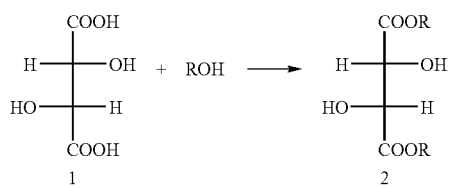

(ii) under the catalysis of a protic acid or Lewis acid such as toluene-p-sulfonic acid or boron trifluoride, compound 2 is reacted by reflux with a ketone of formula R3C(O)R4 wherein R3 and R4 are $C_1$-$C_4$ alkyl, such as acetone, in an inert solvent such as THF or toluene, to obtain a ketal compound 3;

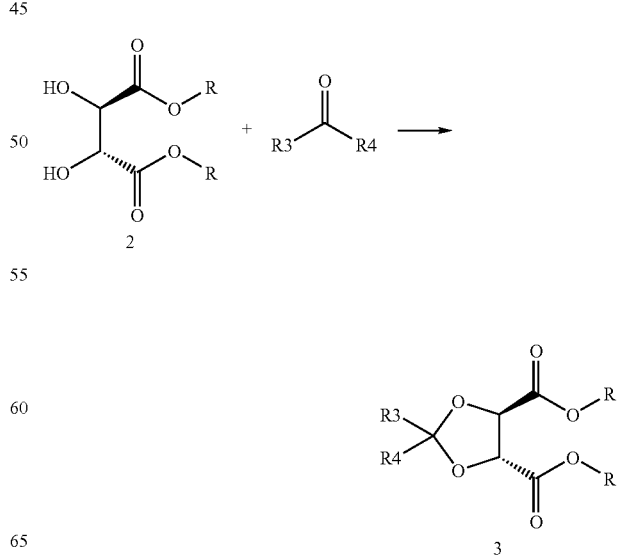

(iii) compound 3 is dissolved in an organic solvent such as THF or dioxane, and is reacted with an aqueous solution of a base such as sodium hydroxide or potassium hydroxide (having a concentration of 1N, and used in a molar ratio of 1:1 in relative to compound 3) at 0° C. to room temperature, and then acidified with an inorganic acid such as hydrochloric acid (having a concentration of 1N), and further extracted with an organic solvent such as dichloromethane, diethyl ether or ethyl acetate, to obtain compound 4;

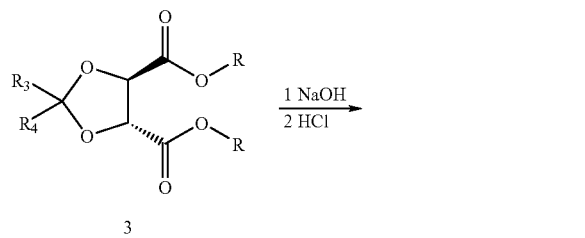

(iv) compound 4 is dissolved in a suitable solvent such as THF, dichloromethane or N,N-dimethylformamide, and, under the catalysis of a suitable amount of dicyclohexylcarbodiimide, camphorsulfonic acid and 4-dimethylaminopyridine, is acylated with $ArNH_2$, to obtain compound 5;

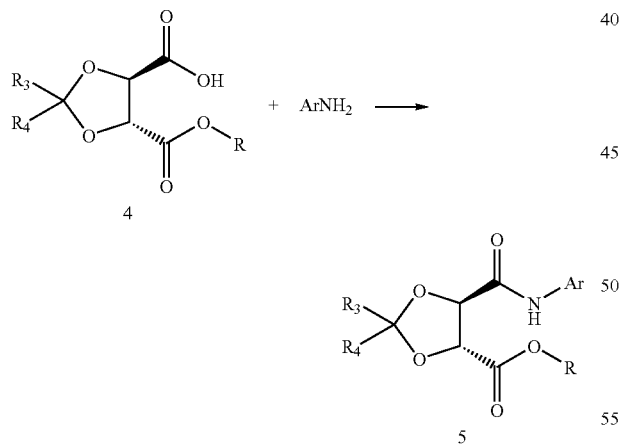

(v) compound 5 is dissolved in an organic solvent such as THF or dioxane, and is reacted with an aqueous solution of a base such as sodium hydroxide or potassium hydroxide (having a concentration of 1N, and used in a molar ratio of 1:1 in relative to compound 5) at 0° C. to room temperature, and then acidified with an inorganic acid such as hydrochloric acid (having a concentration of 1N), and further extracted with an organic solvent such as dichloromethane, diethyl ether or ethyl acetate, to obtain compound 6;

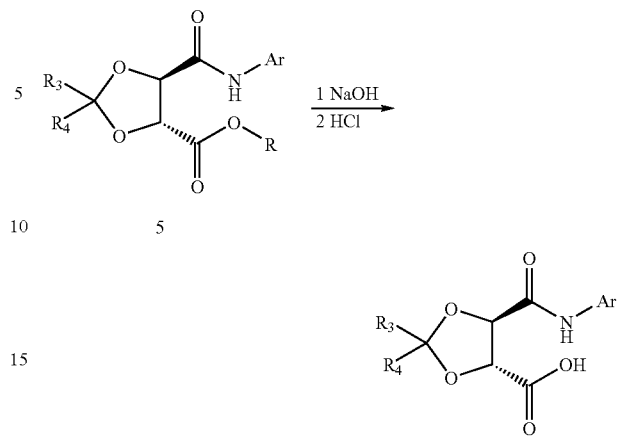

(vi) compound 6 is dissolved in a suitable solvent such as THF, dichloromethane or N,N-dimethylformamide, and, under the catalysis of a suitable amount of dicyclohexylcarbodiimide, camphorsulfonic acid and 4-dimethylaminopyridine, is esterified or acylated with R1ZH (alcohol or amine), wherein R1 and Z are as defined above, to obtain compound 7;

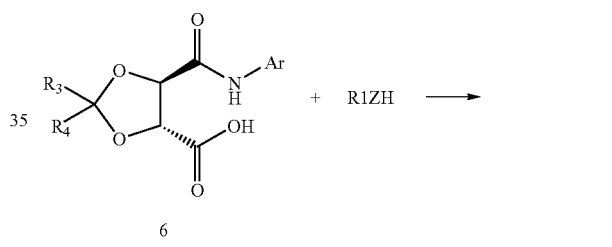

(vii) compound 7 is dissolved in a suitable solvent such as methanol or ethanol, and, under the catalysis of a suitable amount of a protic acid such as hydrochloric acid or sulfuric acid, is deprotected to remove acetonide group, to obtain a specific compound of formula Ib of the invention.

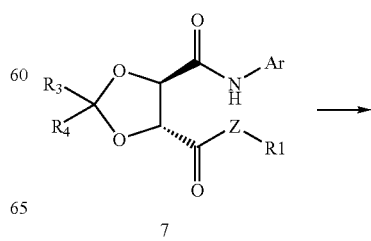

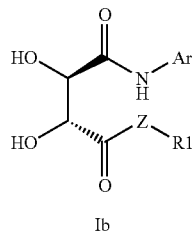

As for more detailed information about the preparation of the compound of formula I of the invention, please see the examples.

In one further aspect, the present invention provides a pharmaceutical composition, comprising a compound of formula I, or all possible isomers, prodrugs, pharmaceutically acceptable salts, solvates or hydrates thereof, and at least one pharmaceutically acceptable carrier or excipient.

In one still further aspect, the present invention relates to use of a compound of formula I, or all possible isomers, prodrugs, pharmaceutically acceptable salts, solvates or hydrates thereof for the manufacture of a medicament for treating and preventing diseases induced by aggregation or deposition of Aβ, the diseases including, but not limited to, Alzheimer's disease, amyloid degenerative angiopathy, Kuru's disease and Down's syndrome.

The compound of formula I or pharmaceutically acceptable salts thereof may be used alone, or together with a pharmaceutically acceptable carrier or excipient in the form of a pharmaceutical composition. When used in the form of a pharmaceutical composition, an effective amount of the compound of formula I or its pharmaceutically acceptable salt and one or more pharmaceutically acceptable carrier or excipient are combined and made into an appropriate administration form or dosage form by means of mixing, granulating, compressing or dissolving the components in suitable mode.

The pharmaceutical composition comprising the compound of the invention may be administered in any of the following routes: orally, inhaled by spray, rectally, nasally, vaginally, topically, parenterally such as subcutaneous, intravenous, intramuscular, intraperitoneal, intrathecal, intraventricular, intrasternal or encephalic injection or infusion, or administered with the aid of an explanted reservoir, wherein the administration routes by orally, intramuscular, intraperitoneal or intravenous injection are preferred. In addition, in order to enable the compound of the invention or the pharmaceutical composition comprising it to be effective for treating neutral nerve system, the intraventricular administration route is preferred to thereby surmount a possible relatively low blood-brain barrier transmissivity of the compound.

The compound of the invention or the pharmaceutical composition comprising the compound of the invention may be administered in a unit dosage form. The dosage form may be in a liquid form, or a solid form. The liquid form includes true solution, colloids, particulates, emulsions, suspensions. Other forms include tablets, capsules, dropping pills, aerosols, pills, powder, solutions, suspensions, emulsions, granules, suppository, lyophilized powder for injection, clathrates, implants, patches, liniment, and etc.

The pharmaceutical composition of the invention may further comprise a commonly used carrier that includes, but not limited to, ion exchanger, alumina, aluminum stearate, lecithin, serum protein such as human serum protein, buffer such as phosphate, glycerin, sorbic acid, potassium sorbate, a mixture of partial glycerine esters of saturated vegetable fatty acids, water, salt or electrolyte, such as protamine sulfate, disodium hydrogen phosphate, potassium hydrogen phosphate, sodium chloride, zinc salt, colloidal silica, magnesium trisilicate, polyvinylpyrrolidone, cellulose, polyethylene glycol, sodium carboxymethylcellulose, polyacrylate, beeswax, lanolin, and etc. The amount of the carrier in the pharmaceutical composition may be 1% to 98% by weight, usually about 80% by weight. For the convenience, topical anesthetic, antiseptic, buffer and etc. may be directly dissolved in the carrier.

Oral tablets and capsules may comprise excipients e.g., binders such as syrup, Arabic gum, sorbitol, tragacanth, or polyvinylpyrrolidone, fillers such as lactose, sucrose, corn starch, calcium phosphate, sorbitol, aminoacetic acid, lubricant such as magnesium stearate, saponite, polyethylene glycol, silica, disintegrating agent such as potato starch, or acceptable moisturizing agent such as sodium lauryl sulfate. Tablets may be coated by using known methods in pharmaceutics.

Oral solution may be made as a suspension of water and oil, a solution, an emulsion, a syrup or an elixir, or made as a dried product to which water or other medium is added before use. This liquid preparation may comprise conventional additives, e.g., suspending agent such as sorbitol, cellulose diethyl ether, glucose syrup, gelatin, hydroxyethyl cellulose, carboxymethyl cellulose, aluminum stearate gel, hydrogenated edible grease; emulsifying agent such as lecithin, sorbitan monooleate, Arabic gum; or non-aqueous carrier (possibly including edible oil), such as almond oil, grease such as glycerin, ethylene glycol, or ethanol; antiseptic such as methyl or propyl p-hydroxybenzoate, sorbic acid. If desired, a flavoring agent or a colorant may be added.

Suppository may comprise a conventional suppository substrate, and the excipient, such as cocoa butter, other glyceride or beewax, is in solid state at room temperature, while melts to release drug at body temperature.

For non-gastric administration, the liquid dosage form is usually made of the compound and a sterilized carrier. The preferred carrier is water. According to the carrier selected and the drug concentration, the compound can be dissolved in the carrier or made into a suspension. When making an injection solution, the compound is firstly dissolved in water, and then filtered and sterilized before being packaged into an enclosed bottle or ampoule.

For topical application on skin, the compound of the invention may be made into a suitable form of ointment, lotion or cream, wherein the active ingredient is suspended or dissolved in one or more carrier(s). The carrier used for an ointment includes, but not limited to, mineral oil, liquid vaseline, white vaseline, propylene glycol, polyoxyethylene, polyoxypropylene, emulsified wax and water; the carrier used for a lotion and a cream includes, but not limited to, mineral oil, sorbitan monostearic ester, Tween 60, cetyl esters wax, hexadecylene aromatic alcohol, 2-octyl dodecanol, benzanol and water.

According to the administration mode, the medicament may contain 0.1% by weight, or more suitably 10% to 60% by weight, of an active ingredient. Nevertheless, when the medicament includes unit dosages, each of the unit dosages had better comprise 1 to 500 mg of an active ingredient.

Further, the administration dosage and manner of the compound described therein directed to different patients depend on various factors, such as age, body weight, gender, natural health status and nutrient status of the patient, active strength of the compound, administration time, metabolic rate, degree of severity of the disease, and subjective judgment made by the doctor for diagnosis/treatment. The preferred administration dosage is within 0.01 to 100 mg/kg body weight/day.

It shall be understood that the optimum administration dosage and interval of compound of formula I are determined by the property of the compound and external conditions such as administration form, route and site, and the optimum administration dosage can be determined according to a conventional technique. Meanwhile, it shall also be understood that the optimum period of treatment, i.e., the dosage of the compound of formula I per day within a predetermined time of period, may be determined by a well-known method in the art.

MODE OF CARRYING OUT THE INVENTION

The following examples are preferred embodiments of the invention, and shall not be understood to limit the present invention in any manner.

The melting point of the compound was determined by using RY-1 melting point apparatus, the thermometer being not calibrated. Mass spectrum was determined by using Micromass ZabSpec high resolution mass spectrometer (resolution 1000). $^1$H NMR was determined by using JNM-ECA-400 superconductive NMR spectrometer, the working frequency being $^1$H NMR 400 MHz. Specific rotation was determined by using PE-243B polarimeter, $\lambda_{Na}$=589 nm, the temperature being 20° C.

Example 1

Preparation of methyl L-(2R,3R)-2-[2,3-diacetoxy-3-(naphthalen-2-ylcarbamoyl)-propionylamino]-3-phenyl-propionate

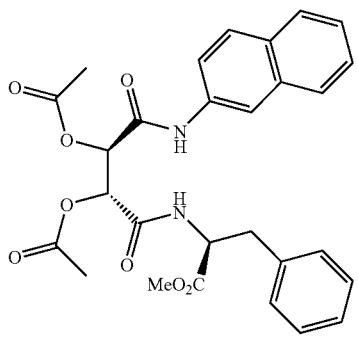

Step 1 Preparation of L-(4R,5R)-2,3-diacetoxy-succinic anhydride 10.00 g (66.7 mmol) L-tartaric acid was dissolved in 31.5 ml acetic anhydride, to which was added 0.3 ml concentrated sulfuric acid with stirring; the resulting mixture was slowly heated till to reflux, and continuously stirred for 40 minutes, followed by cooling down to room temperature; a solid was precipitated, filtered, and washed with anhydrous diethyl ether, to obtain 10.00 g of a yellowish solid, yield 69.4%.

Step 2 Preparation of L-(2R,3R)-2,3-diacetoxy-3-(naphthalen-2-ylcarbamoyl)-propionic acid 3.30 g (15.3 mmol) L-(4R,5R)-2,3-diacetoxy-succinic anhydride was dissolved in 20 ml dichloromethane, to which, in ice bath, was added dropwise 2.19 g (15.3 mmol) 2-naphthylamine dissolved in 6 ml dichloromethane, followed by stirring for 4 hours, till completion of reaction. The resulting reaction product was alkalified with a 4% sodium bicarbonate solution to a pH of about 8, and extracted with $CH_2Cl_2$ twice; the obtained organic phases were discarded; the remaining water phase was adjusted with 1 M HCl to a pH value of 1 to 2, and extracted with $CH_2Cl_2$ for three times, then the obtained organic phases were combined, dried with anhydrous $Na_2SO_4$, and subjected to solvent removal by evaporation, to thereby obtain 4.60 g of a white solid, yield 83.9%. $^1$H-NMR (DMSO, 400 MHz), δ (ppm): 2.00 (3H, s, $CH_3$), 2.06 (3H, s, $CH_3$), 5.65 (1H, d, J=2.80 Hz, CH), 5.74 (1H, d, J=2.80 Hz, CH), 7.43 (1H, t, J=8.12 Hz, ArH), 7.49 (1H, t, J=8.40 Hz, ArH), 7.58 (1H, d, J=8.96 Hz, ArH), 7.87 (3H, m, ArH), 8.21 (1H, s, ArH), 10.43 (1H, s, CONH), 13.85 (1H, br, COOH); FAB-MS m/e (%): 360.1 ([M+1]$^+$, 100), 318 (32).

Step 3 Preparation of methyl L-(2R,3R)-2-[2,3-diacetoxy-3-(naphthalen-2-ylcarbamoyl)-propionylamino]-3-phenyl-propionate 0.36 g (1.0 mmol) L-(2R,3R)-2,3-diacetoxy-3-(naphthalen-2-ylcarbamoyl)-propionic acid and 0.22 g (1.0 mmol) methyl L-phenprobamate hydrochloride were dissolved in 10 ml anhydrous THF, to which were further added 0.20 g (1.5 mmol) HOBt, 0.12 g (1.0 mmol) triethylamine and 0.31 g (1.5 mmol) DCC, followed by reacting at room temperature with stirring for 2 hours; the solid resulted from the reaction was removed by filtration; the remaining mother liquor was evaporated to dryness under reduced pressure to obtain an oily matter, which was loaded on a silica gel chromatographic column, and eluted with cyclohexane:ethyl acetate=2:1, to obtain 0.22 g of a white solid, yield 41.4%, specific rotation $[\alpha]_D^{20}$=−14.3° (20 mg/2 ml, DMF). $^1$H-NMR (DMSO, 400 MHz), δ (ppm): 2.10 (3H, s, $CH_3$), 2.13 (3H, s, $CH_3$), 3.05 (2H, m, $CH_2$), 3.66 (3H, s, $CH_3$), 4.49 (1H, m, CH), 5.54 (1H, d, J=2.52 Hz, CH), 5.66 (1H, d, J=2.56 Hz, CH), 7.18-7.24 (5H, m, ArH), 7.43 (1H, t, J=7.00 Hz, ArH), 7.48 (1H, t, J=6.72 Hz, ArH), 7.58 (1H, m, ArH), 7.85 (3H, m, ArH), 8.17 (1H, d, J=1.96 Hz, ArH), 8.59 (1H, d, J=8.12 Hz, CONH), 10.39 (1H, s, CONH); HREI-MS Calcd. for $C_{28}H_{28}N_2O_8$: 520.1846. found: 520.1831.

Example 2

Preparation of methyl L-(2R,3R)-4-{[2,3-diacetoxy-3-(4-phenoxy-phenylcarbamoyl)-propionylamino]methyl}-benzoate

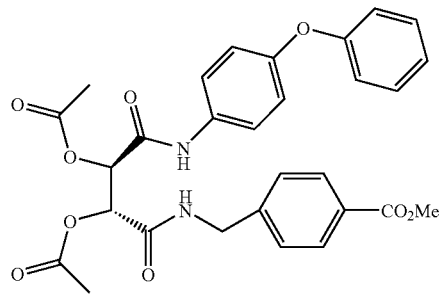

Step 1 Preparation of L-(2R,3R)-2,3-diacetoxy-3-(4-phenoxy-phenylcarbamoyl)propionic acid According to the procedures in Step 2 of Example 1, 7.49 g (34.6 mmol) L-(4R,5R)-2,3-diacetoxy-succinic anhydride and 6.41 g (34.6 mmol) p-phenoxyaniline were reacted to obtain 8.97 g of a grey solid, yield 64.8%, specific rotation $[\alpha]_D^{20}=-10.3°$ (20 mg/2 ml, $CH_3OH$). $^1$H-NMR (DMSO, 400 MHz), δ (ppm): 2.06 (3H, s, $CH_3$), 2.13 (3H, s, $CH_3$), 5.58 (1H, d, J=2.80 Hz, CH), 5.64 (1H, d, J=3.08 Hz, CH), 6.90 (4H, m, ArH), 7.12 (1H, t, J=7.28 Hz, ArH), 7.37 (2H, t, J=7.56 Hz, ArH), 7.55 (2H, d, J=8.96 Hz, ArH), 10.24 (1H, s, CONH), 13.88 (1H, br, COOH); FAB-MS m/e (%): 402.1 ([M+1]$^+$, 100), 360.0 (36).

Step 2 Preparation of methyl L-(2R,3R)-4-{[2,3-diacetoxy-3-(4-phenoxy-phenylcarbamoyl)-propionylamino]methyl}-benzoate 2.00 g (5.00 mmol) L-(2R,3R)-2,3-diacetoxy-3-(4-phenoxy-phenylcarbamoyl)propionic acid and 1.01 g (5.00 mmol) methyl 4-aminomethylbenzoate hydrochloride were reacted according to the procedures of synthesizing compound (1), to obtain 1.60 g of a white solid, yield 58.3%, specific rotation $[\alpha]_D^{20}=+7.5°$ (20 mg/2 ml, DMF). $^1$H-NMR (DMSO, 400 MHz), δ (ppm): 2.07 (3H, s, $CH_3$), 2.11 (3H, s, $CH_3$), 3.84 (3H, s, $CH_3$), 4.31 (1H, m, ×$CH_2$), 4.51 (1H, m, ×$CH_2$), 5.58 (1H, d, J=2.52 Hz, CH), 5.75 (1H, d, J=2.80 Hz, CH), 6.98 (4H, m, ArH), 7.11 (1H, t, J=7.60 Hz, ArH), 7.38 (4H, m, ArH), 7.52 (2H, d, J=8.96 Hz, ArH), 7.93 (2H, d, J=8.40 Hz, ArH), 8.86 (1H, t, J=6.16 Hz, CONH), 10.27 (1H, s, CONH); HREI-MS Calcd. for $C_{29}H_{28}N_2O_9$: 548.1791. found: 548.1791.

Example 3

Preparation of methyl L-(2R,3R)-4-[2,3-diacetoxy-3-(4-phenoxy-phenylcarbamoyl)-propionylamino]-butyrate

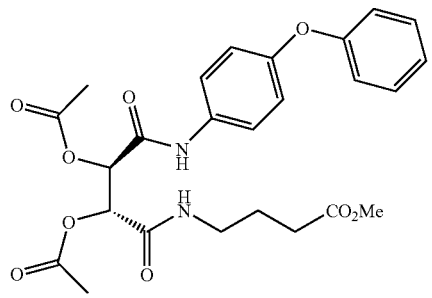

2.00 g (5.00 mmol) L-(2R,3R)-2,3-diacetoxy-3-(4-phenoxy-phenylcarbamoyl)propionic acid prepared in Example 2 and 0.77 g (5.00 mmol) methyl 4-aminobutyrate hydrochloride were reacted according to the procedures of synthesizing compound (1), to obtain 1.20 g of a white solid, yield 48.0%, specific rotation $[\alpha]_D^{20}=+8.1°$ (20 mg/2 ml, DMF). $^1$H-NMR ($CDCl_3$, 400 MHz), δ (ppm): 1.85 (2H, m, $CH_2$), 2.20 (6H, s, 2×$CH_3$), 2.37 (2H, m, $CH_2$), 3.34 (2H, m, $CH_2$), 3.66 (3H, s, $CH_3$), 5.74 (2H, s, 2×CH), 6.89 (1H, br, CONH), 6.97 (4H, m, ArH), 7.08 (1H, t, J=7.56 Hz, ArH), 7.32 (2H, t, J=8.12 Hz, ArH), 7.44 (2H, d, J=8.56 Hz, ArH), 8.54 (1H, br, CONH); HREI-MS Calcd. for $C_{25}H_{28}N_2O_9$: 500.1795. found: 500.1780.

Example 4

Preparation of methyl L-(2R,3R)-4-{[3-(3-di-n-propylaminoformyl-phenylcarbamoyl)-2,3-diacetoxy-propionylamino]methyl}-benzoate

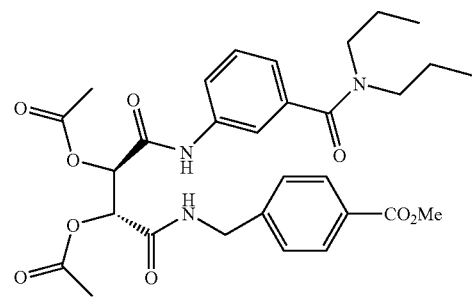

Step 1 Preparation of L-(2R,3R)-2,3-diacetoxy-3-(3-di-n-propylaminoformyl-phenylcarbamoyl)propionic acid According to the procedures in Step 2 of Example 1, 5.2 g (24.1 mmol) L-(4R,5R)-2,3-diacetoxy-succinic anhydride and 5.30 g (24.1 mmol) p-phenoxyaniline were reacted, to obtain 6.40 g of a yellowish solid, yield 62.7%, specific rotation $[\alpha]_D^{20}=-10.1°$ (20 mg/2 ml, $CH_3OH$). $^1$H-NMR (DMSO, 400 MHz), δ (ppm): 0.67 (3H, s, $CH_3$), 0.90 (3H, s, $CH_3$), 1.46 (2H, s, $CH_2$), 1.58 (2H, s, $CH_2$), 2.05 (3H, s, $CH_3$), 2.15 (3H, s, $CH_3$), 3.10 (2H, s, $CH_2$), 3.33 (2H, s, $CH_2$), 3.91 (3H, s, $CH_3$), 5.58 (1H, d, J=3.08 Hz, CH), 5.67 (1H, d, J=2.80 Hz, CH), 7.04 (1H, d, J=7.56 Hz, ArH), 7.38 (1H, t, J=7.84 Hz, ArH), 7.54 (2H, d, J=8.96 Hz, ArH), 10.32 (1H, s, CONH), 13.74 (1H, br, COOH); FAB-MS m/e (%): 437.1 ([M+1]$^+$, 100), 335.9 (16).

Step 2 Preparation of methyl L-(2R,3R)-4-{[3-(3-di-n-propylaminoformyl-phenylcarbamoyl)-2,3-diacetoxy-propionylamino]methyl}-benzoate 1.50 g (3.44 mmol) L-(2R,3R)-2,3-diacetoxy-3-(3-di-n-propylaminoformyl-phenylcarbamoyl)propionic acid and 0.70 g (3.44 mmol) methyl 4-aminomethylbenzoate hydrochloride were reacted according to the procedures of synthesizing compound (1), to obtain 1.20 g of a white solid, yield 59.8%, specific rotation $[\alpha]_D^{20}=+17.8°$ (20 mg/2 ml, DMF). $^1$H-NMR ($CDCl_3$, 400 MHz), δ (ppm): 0.73 (3H, t, J=7.32 Hz, $CH_3$), 0.96 (3H, t, J=7.28 Hz, $CH_3$), 1.51 (2H, m, $CH_2$), 1.66 (2H, m, $CH_2$), 2.10 (3H, s, $CH_3$), 2.11 (3H, s, $CH_3$), 3.13 (2H, t, J=7.60 Hz, $CH_2$), 3.40 (2H, m, $CH_2$), 4.38 (1H, m, ×$CH_2$), 4.58 (1H, m, ×$CH_2$), 5.78 (1H, d, J=3.12 Hz, CH), 5.80 (1H, d, J=3.08 Hz, CH), 7.06 (1H, d, J=7.56 Hz, ArH), 7.25-7.31 (4H, m, ArH), 7.40 (1H, br, CONH), 7.54 (1H, d, J=8.12 Hz, ArH), 7.96 (2H, d, J=8.12 Hz, ArH), 8.90 (1H, br, CONH); FAB-MS m/e (%): 584.0 ([M+1]$^+$, 100).

Example 5

Preparation of dimethyl L-(2R,3R)-5-[2,3-diacetoxy-3-(1-methoxycarbonyl-2-phenyl-ethylcarbamoyl)-propionylamino]-isophthalate

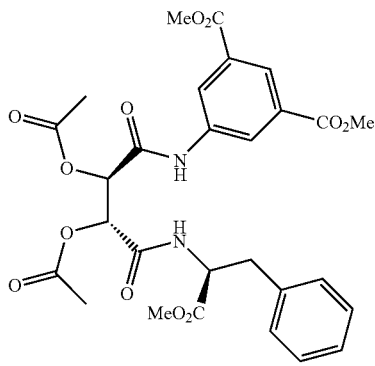

Step 1 L-(2R,3R)-2,3-diacetoxy-3-(3,5-dimethoxy-carbonylphenylcarbamoyl)propionic acid According to the procedures in Step 2 of Example 1, 7.43 g (34.4 mmol) L-(4R,5R)-2,3-diacetoxy-succinic anhydride and 7.20 g (24.1 mmol) dimethyl 5-amino-isophthalate were reacted, to obtain 10.00 g of a yellowish oily matter, yield 70.1%, specific rotation $[\alpha]_D^{20}$=−6.3° (20 mg/2 ml, CH$_3$OH). $^1$H-NMR (DMSO, 400 MHz), δ (ppm): 2.06 (3H, s, CH$_3$), 2.16 (3H, s, CH$_3$), 3.90 (6H, s, 2×CH$_3$), 5.61 (1H, d, J=2.80 Hz, CH), 5.69 (1H, d, J=3.08 Hz, CH), 8.21 (1H, s, ArH), 8.48 (2H, s, ArH), 10.69 (1H, s, CONH), 13.77 (1H, br, COOH); FAB-MS m/e (%): 426.0 ([M+1]$^+$, 100), 384.0 (22).

Step 2 Preparation of dimethyl L-(2R,3R)-5-[2,3-diacetoxy-3-(1-methoxycarbonyl-2-phenyl-ethylcarbamoyl)-propionylamino]-isophthalate 1.50 g (3.53 mmol) L-(2R,3R)-2,3-diacetoxy-3-(3,5-dimethoxycarbonylphenyl carbamoyl)propionic acid and 0.76 g (3.53 mmol) methyl L-phenprobamate hydrochloride were reacted according to the procedures of synthesizing compound (1), to obtain 1.10 g of a white solid, yield 53.2%, specific rotation $[\alpha]_D^{20}$=−8.1° (20 mg/2 ml, DMF). $^1$H-NMR (CDCl$_3$, 400 MHz), δ (ppm): 2.05 (3H, s, CH$_3$), 2.21 (3H, s, CH$_3$), 3.14 (2H, m, CH$_2$), 3.76 (3H, s, CH$_3$), 3.95 (6H, s, 2×CH$_3$), 4.91 (1H, m, CH), 5.78 (1H, d, J=3.36 Hz, CH), 5.80 (1H, d, J=3.04 Hz, CH), 6.57 (1H, d, J=8.12 Hz, CONH), 706 (2H, m, ArH), 7.27 (3H, m, ArH), 7.38 (2H, d, J=1.40 Hz, ArH), 8.43 (1H, br, CONH), 8.45 (1H, s, ArH); HREI-MS Calcd. for C$_{28}$H$_{30}$N$_2$O$_{12}$: 586.1799. found: 586.1777.

Example 6

Preparation of dimethyl L-(2R,3R)-5-[2,3-diacetoxy-3-(4-methoxycarbonyl-benzylcarbamoyl)-propionylamino]-isophthalate

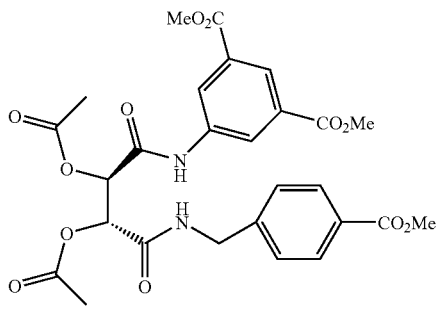

1.50 g (3.53 mmol) of L-(2R,3R)-2,3-diacetoxy-3-(3,5-dimethoxycarbonyl phenylcarbamoyl)propionic acid prepared in Example 5 and 0.71 g (3.53 mmol) methyl 4-aminomethylbenzoate hydrochloride were reacted according to the procedures of synthesizing compound (1), to obtain 0.42 g of a white solid, yield 20.8%. $^1$H-NMR (DMSO, 400 MHz), δ (ppm): 2.10 (6H, s, 2×CH$_3$), 3.84 (3H, s, CH$_3$) 3.90 (6H, s, 2×CH$_3$), 4.33 (1H, m, ×CH$_2$), 4.50 (1H, m, ×CH$_2$), 5.60 (1H, d, J=2.80 Hz, CH), 5.77 (1H, d, J=3.08 Hz, CH), 7.38 (2H, d, J=8.40 Hz, ArH), 7.91 (2H, d, J=8.12 Hz, ArH), 7.90 (1H, d, J=1.40 Hz, ArH), 8.45 (2H, d, J=1.40 Hz, ArH), 8.89 (1H, t, J=6.16 Hz, CONH), 8.89 (1H, s, CONH); HREI-MS Calcd. for C$_{27}$H$_{28}$N$_2$O$_{12}$: 572.1642. found: 572.1661.

Example 7

Preparation of L-(2R,3R)—N-benzyl-2,3-diacetoxy-3-(4-benzyl-piperazin-1-yl-formyl)-propionamide

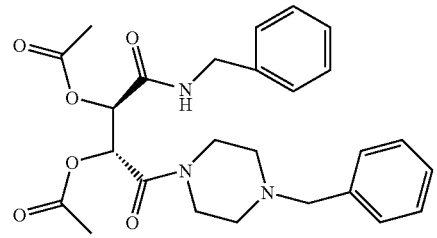

Step 1 Preparation of L-(2R,3R)-2,3-diacetoxy-3-(benzylcarbamoyl)propionic acid

According to the procedures in Step 2 of Example 1, 2.16 g (10.0 mmol) L-(4R,5R)-2,3-diacetoxy-succinic anhydride and 1.07 g (10.0 mmol) benzylamine were reacted, to obtain 2.80 g of a white solid, yield 86.7%. $^1$H-NMR (DMSO, 400 MHz), δ (ppm): 2.00 (3H, s, CH$_3$), 2.12 (3H, s, CH$_3$), 4.23 (1H, m, ×CH$_2$), 4.37 (1H, m, ×CH$_2$), 5.52 (1H, d, J=2.52 Hz, CH), 5.54 (1H, d, J=2.52 Hz, CH), 7.19-7.31 (5H, m, ArH), 8.76 (1H, t, J=6.16 Hz, CONH), 13.70 (1H, br, COOH); FAB-MS m/e (%): 324.0 ([M+1]$^+$, 100), 91.0 (20).

Step 2 Preparation of L-(2R,3R)—N-benzyl-2,3-diacetoxy-3-(4-benzyl-piperazin-1-yl-formyl)-propionamide 1.24 g (3.83 mmol) L-(2R,3R)-2,3-diacetoxy-3-(benzylcarbamoyl)propionic acid and 0.67 g (3.83 mmol) 4-benzylpiperazine were reacted according to the procedures of synthesizing compound (1), to obtain 0.80 g of a white solid, yield 43.4%. $^1$H-NMR (CDCl$_3$, 400 MHz), δ (ppm): 1.94 (1H, m, ×CH$_2$), 2.06 (3H, s, CH$_3$), 2.15 (3H, s, CH$_3$), 2.40 (2H, m, CH$_2$), 2.42 (2H, m, CH$_2$), 3.34 (1H, br, ×CH$_2$), 3.61 (3H, s, CH$_3$), 3.64 (2H, s, CH$_2$), 4.35 (1H, m, ×CH$_2$), 4.64 (1H, m, ×CH$_2$), 5.66 (1H, d, J=3.64 Hz, CH), 5.87 (1H, d, J=3.64 Hz, CH), 6.72 (1H, t, J=6.04 Hz, CONH), 7.27-7.33 (10H, m, ArH); FAB-MS m/e (%): 482.0 ([M+1]$^+$, 100).

Example 8

Preparation of methyl L-(2R,3R)-4-[(3-benzylcarbamoyl-2,3-dihydroxy-propionylamino)methyl]-benzoate

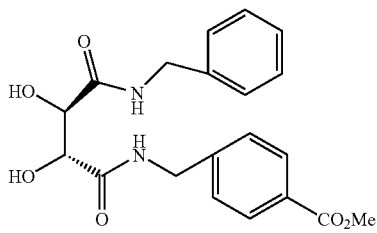

Step 1 Preparation of L-(4R,5R)-2,2-dimethyl-1,3-dioxolane-4,5-dicarboxylic monomethyl ester 8.59 g (39.4 mmol) L-(4R,5R)-2,2-dimethyl-1,3-dioxolane-4,5-dicarboxylic dimethyl ester was dissolved in 200 ml water/dioxane (volume ratio of 1:1) mixed solvent, to which was slowly added dropwise 39.4 ml 1 M NaOH within 30 minutes, followed by reacting with stirring at room temperature for 1 hour; the resulting reaction product was extracted with $CH_2Cl_2$ for three times; the obtained organic phases were discarded; the remaining water phase was adjusted with 1 M HCl to a pH value of 2 to 3, and extracted with $CH_2Cl_2$ for three times; the obtained organic phases were combined, dried with anhydrous $Na_2SO_4$, subjected to solvent removal by evaporation, loaded on a silica gel chromatographic column, and eluted in sequence with petroleum ether:ethyl acetate=5:1, and with ethyl acetate, to thereby obtain 6.8 g of a yellowish oily matter, yield 84.6%, specific rotation $[\alpha]_D^{20}=-51.2°$ (20 mg/2 ml, $CH_3OH$). $^1$H-NMR ($CDCl_3$, 400 MHz), δ (ppm): 1.50 (3H, s, $CH_3$), 1.52 (3H, s, $CH_3$), 3.84 (2H, s, $CH_2$), 4.83 (1H, d, J=5.60 Hz, CH), 4.89 (1H, d, J=5.64 Hz, CH), 9.76 (1H, br, OH).

Step 2 Preparation of methyl L-(4R,5R)-5-benzylaminocarbonyl-2,2-dimethyl-1,3-dioxolane-4-formate 6.0 g (29.4 mmol) L-(4R,5R)-2,2-dimethyl-1,3-dioxolane-4,5-dicarboxylic monomethyl ester and 3.78 g (35.2 mmol) benzylamine were dissolved in 140 ml anhydrous THF, to which were further added 5.96 g (44 mol) HOBt, and 9.08 g (44 mol) DCC, followed by reacting at room temperature for 2 hours; solid matter resulted from the reaction was removed by filtration; the remaining mother liquor was evaporated to dryness under reduced pressure to obtain an oily matter, which was loaded on a silica gel chromatographic column, and eluted with petroleum ether:ethyl acetate=3:1, to obtain 7.8 g of a colorless oily matter, yield 86.4%. $^1$H-NMR ($CDCl_3$, 400 MHz), δ (ppm): 1.33 (3H, t, $J_{HH}$=7.00 Hz, $CH_3$), 1.45 (3H, s, $CH_3$), 1.46 (3H, s, $CH_3$), 4.30 (2H, q, J=7.00 Hz, $CH_2$), 4.44-4.55 (2H, m, $CH_2$), 4.77 (1H, d, J=5.52 Hz, CH), 4.82 (1H, d, J=5.30 Hz, CH), 6.82 (1H, br, CONH), 7.26-7.38 (5H, m, ArH).

Step 3 Preparation of L-(4R,5R)-5-benzylaminocarbonyl-2,2-dimethyl-1,3-dioxolane-4-formic acid 7.56 g (24.6 mmol) methyl of L-(4R,5R)-5-benzylaminocarbonyl-2,2-dimethyl-1,3-dioxolane-4-formate was dissolved in 300 ml water/dioxane (volume ratio of 1:1) mixed solvent, to which was slowly added dropwise 24.6 ml 1 M NaOH within 30 minutes, followed by reacting with stirring at room temperature for 1 hour; the resulting reaction product was extracted with $CH_2Cl_2$ for three times; the obtained organic phases were discarded; the remaining water phase was adjusted with 1 M HCl to a pH value of 2, and extracted with $CH_2Cl_2$ for three times; the obtained organic phases were combined, dried with anhydrous $Na_2SO_4$, and subjected to solvent removal by evaporation, to thereby obtain 6.5 g of a yellowish oily matter, yield 94.4%. $^1$H-NMR ($CDCl_3$, 400 MHz), δ (ppm): 1.46 (3H, s, $CH_3$), 1.51 (3H, s, $CH_3$), 4.58-4.65 (4H, m, $CH_2$ and 2×CH), 7.30 (1H, br, CONH), 7.31-7.37 (5H, m, ArH), 11.25 (1H, br, OH).

Step 4 Preparation of methyl L-(4R,5R)-4-{[(5-benzylaminocarbonyl-2,2-dimethyl-1,3-dioxolane-4-formyl)amino]-methyl}benzoate 0.28 g (1.0 mmol) L-(4R,5R)-5-benzylaminocarbonyl-2,2-dimethyl-1,3-dioxolane-4-formic acid and 0.20 g (1.0 mmol) methyl 4-aminomethylbenzoate hydrochloride were dissolved in 10 ml anhydrous THF, to which were further added 0.20 g (1.5 mmol) HOBt, 0.12 g (1.0 mmol) triethylamine and 0.31 g (1.5 mmol) DCC, followed by reacting at room temperature with stirring for 2 hours; solid matter resulted from the reaction was removed by filtration; the remaining mother liquor was evaporated to dryness under reduced pressure to obtain an oily matter, which was loaded on a silica gel chromatographic column, and eluted with cyclohexane:ethyl acetate=3:1, to obtain 0.25 g of a colorless oily matter, yield 58.5%, specific rotation $[\alpha]_D^{20}=-33.8°$ (20 mg/2 ml, $CH_3OH$). $^1$H-NMR (DMSO, 400 MHz), δ (ppm): 1.41 (6H, s, 2×$CH_3$), 3.84 (3H, m, $CH_3$), 4.33 (2H, t, J=6.16 Hz, $CH_2$), 4.40 (2H, t, J=6.16 Hz, $CH_2$), 4.59 (1H, d, J=6.44 Hz, CH), 4.63 (1H, d, J=4.76 Hz, CH), 7.26-7.32 (5H, m, ArH), 7.41 (2H, d, J=8.12 Hz, ArH), 7.91 (2H, d, J=8.12 Hz, ArH), 8.71 (1H, t, J=6.16 Hz, CONH), 8.83 (1H, t, J=6.16 Hz, CONH); FAB-MS m/e (%): 427.1 ([M+1]$^+$, 100), 91.2 (32).

Step 5 Preparation of methyl L-(2R,3R)-4-[(3-benzylcarbamoyl-2,3-dihydroxy-propionylamino)methyl]-benzoate 0.20 g (0.47 mmol) methyl L-(4R,5R)-4-{[(5-benzylaminocarbonyl-2,2-dimethyl-1,3-dioxolane-4-formyl)amino]-methyl}benzoate was dissolved in 10 ml methanol, to which was added 0.5 ml 1 N HCl, followed by reacting with reflux for 8 hours; the resulting reaction product was evaporated to dryness under reduced pressure to obtain an oily matter, which was loaded on a silica gel chromatographic column, and eluted with cyclohexane:ethyl acetate=1:1, to obtain 0.10 g of a white solid, yield 55.2%, mp: 205-206° C., specific rotation $[\alpha]_D^{20}=+90.4°$ (20 mg/2 ml, $CH_3OH$). $^1$H-NMR (DMSO, 400 MHz), δ (ppm): 3.84 (3H, s, $CH_3$), 4.28-4.50 (6H, m, 2×$CH_2$ and 2×CH), 5.77 (2H, m, 2×OH), 7.22 (1H, m, ArH), 7.30 (4H, m, ArH), 7.44 (2H, d, J=8.12 Hz, ArH), 7.89 (2H, d, J=8.12 Hz, ArH), 8.71 (1H, t, J=6.16 Hz, CONH), 8.83

(1H, t, J=6.16 Hz, CONH); ELMS m/e (%): 386.1 (M⁺, 40), 194.0 (92), 91.1 (100); HREI-MS Calcd. for $C_{20}H_{22}N_2O_6$: 386.1478. found: 386.1490.

Example 9

Preparation of methyl L-(2R,3R)-2-[(3-benzylcarbamoyl-2,3-dihydroxy-propionylamino)-3-phenyl-propionate

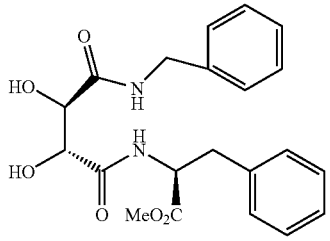

Step 1 Preparation of methyl L-(4R,5R)-5-(naphthyl-2-amino)carbonyl-2,2-dimethyl-1,3-dioxolane-4-formyl-L-phenprobamate According to the procedures in Step 4 of Example 8, 0.56 g (2.0 mmol) L-(4R,5R)-5-benzylaminocarbonyl-2,2-dimethyl-1,3-dioxolane-4-formic acid prepared in Example 8 and 0.44 g (2.0 mmol) methyl L-phenprobamate hydrochloride were reacted, to obtain 0.88 g of a colorless oily matter, exhibiting a single spot by TLC, without further purification, yield 100.0%.

Step 2 Preparation of methyl L-(2R,3R)-2-[(3-benzylcarbamoyl-2,3-dihydroxy-propionylamino)-3-phenyl-propionate 0.60 g (1.36 mmol) methyl L-(4R,5R)-5-(naphthyl-2-amino)carbonyl-2,2-dimethyl-1,3-dioxolane-4-formyl-L-phenprobamate was dissolved in 10 ml methanol, and reacted according to the procedures of synthesizing compound (8), to obtain 0.30 g of a white solid, yield 55.1%, specific rotation $[\alpha]_D^{20}$=+86.4° (20 mg/2 ml, $CH_3OH$). ¹H-NMR (DMSO, 400 MHz), δ (ppm): 3.05 (2H, m, $CH_2$), 3.61 (3H, s, $CH_3$), 4.27-4.40 (4H, m, $CH_2$ and 2×CH), 4.58 (H, m, CH), 5.61 (1H, d, J=7.28 Hz, OH), 5.83 (1H, d, J=7.56 Hz, OH), 7.18-7.29 (10H, m, ArH), 7.90 (1H, d, J=8.12 Hz, CONH), 8.21 (1H, t, J=6.16 Hz, CONH); EI-MS m/e (%): 400.1 (M', 30), 194.0 (62), 91.1 (100); HREI-MS Calcd. for $C_{21}H_{24}N_2O_6$: 400.1634. found: 400.1623.

Example 10

Preparation of L-(2R,3R)-2-(3-benzylcarbamoyl-2,3-dihydroxy-propionylamino)-3-phenyl-propionic acid

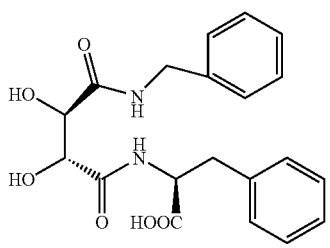

0.20 g (0.50 mmol) methyl L-(2R,3R)-2-(3-benzylcarbamoyl-2,3-dihydroxy-propionylamino)-3-phenyl-propionate prepared in Example 9 was dissolved in 5 ml water/dioxane (volume ratio of 1:1) mixed solvent, to which was added 1 ml 1 N NaOH, followed by reacting with stirring at room temperature for 4 hours; the resulting reaction product was extracted with $CH_2Cl_2$ for three times; the obtained organic phases were discarded; the remaining water phase was adjusted with 1 M HCl to a pH value of 2, and extracted with $CH_2Cl_2$ for three times; the obtained organic phases were combined, dried with anhydrous $Na_2SO_4$, and subjected to solvent removal by evaporation, to thereby obtain 0.07 g of a white solid, yield 36.2%, mp: 236-238° C., specific rotation $[\alpha]_D^{20}$=+118° (20 mg/2 ml, $CH_3OH$). ¹H-NMR (DMSO, 400 MHz), δ (ppm): 3.04 (2H, m, $CH_2$), 4.28-4.39 (4H, m, $CH_2$ and 2×CH), 4.55 (H, m, CH), 5.58 (1H, br, OH), 5.83 (1H, d, J=7.56 Hz, OH), 7.18-7.30 (10H, m, ArH), 7.69 (1H, d, J=7.84 Hz, CONH), 8.21 (1H, t, J=5.88 Hz, CONH), 13.00 (1H, br, COOH); FAB-MS m/e (%): 387.1 ([M+1]⁺, 100), 91.0 (82).

Example 11

Preparation of methyl L-(2R,3R)-4-(3-benzylcarbamoyl-2,3-dihydroxy-propionylaminomethyl)-cyclohexanecarboxylate

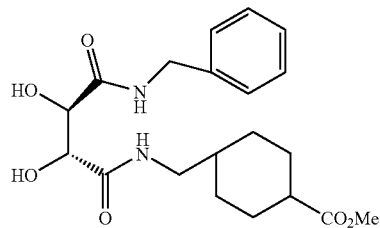

Step 1 Preparation of methyl L-(4R,5R)-4-{[(5-benzylaminocarbonyl-2,2-dimethyl-1,3-dioxolane-4-formyl)amino]-methyl}cyclohexanecarboxylate According to the procedures in Step 4 of Example 8, 0.62 g (2.2 mmol) L-(4R,5R)-5-benzylaminocarbonyl-2,2-dimethyl-1,3-dioxolane-4-formic acid prepared in Example 8 and 0.46 g (2.2 mmol) methyl (4-aminomethyl)cyclohexanecarboxylate hydrochloride were reacted, to obtain 0.42 g of a colorless oily matter, yield 44.2%, specific rotation $[\alpha]_D^{20}$=−34.3° (20 mg/2 ml, $CH_3OH$). ¹H-NMR (DMSO, 400 MHz), δ (ppm): 0.93 (2H, m, $CH_2$), 1.24 (2H, m, $CH_2$), 1.40 (7H, m, 2×$CH_3$ and ½×$CH_2$), 1.69 (2H, d, J=12.6 Hz, $CH_2$), 1.88 (2H, d, J=11.2 Hz, $CH_2$), 2.22 (1H, m, ×$CH_2$), 2.96 (2H, m, $CH_2$), 3.57 (3H, s, $CH_3$), 4.31 (2H, d, J=11.4 Hz, $CH_2$), 4.51 (1H, d, J=6.44 Hz, CH), 4.55 (1H, d, J=6.44 Hz, CH), 7.23-7.31 (5H, m, ArH), 8.14 (1H, t, J=5.48 Hz, CONH), 8.81 (1H, t, J=6.16 Hz, CONH); EI-MS m/e (%): 432.2 (M⁺, 35), 176.1 (84), 91.1 (100).

Step 2 Preparation of methyl L-(2R,3R)-4-(3-benzylcarbamoyl-2,3-dihydroxy-propionylaminomethyl)-cyclohexanecarboxylate 0.40 g (0.93 mmol) methyl L-(4R,5R)-4-{[(5-benzylaminocarbonyl-2,2-dimethyl-1,3-dioxolane-4-formyl)amino]-methyl}cyclohexanecarboxylate was dissolved in 10 ml methanol, and reacted according to the procedures of synthesizing compound (8), to obtain 0.11 g of a white solid, yield 29.4%, mp: 153-154° C., specific rotation $[\alpha]_D^{20}$=+83.9° (20 mg/2 ml, CH$_3$OH). $^1$H-NMR (DMSO, 400 MHz), δ (ppm): 0.92 (2H, m, CH$_2$), 1.26 (2H, m, CH$_2$), 1.42 (1H, m, CH), 1.74 (2H, m, CH$_2$), 1.86 (2H, m, CH$_2$), 2.22 (1H, m, CH), 2.97 (2H, m, CH$_2$), 3.59 (3H, s, CH$_3$), 4.26-4.39 (4H, m, CH$_2$ and 2×CH), 5.60 (2H, m, 2×OH), 7.21 (1H, m, ArH), 7.28 (4H, m, ArH), 7.64 (1H, t, J=6.16 Hz, CONH), 8.19 (1H, t, J=6.44 Hz, CONH); EI-MS m/e (%): 392.1 (M$^+$, 20), 258.1 (92), 91.0 (100); HREI-MS Calcd. for C$_{20}$H$_{28}$N$_2$O$_6$: 392.1947. found: 392.1951.

Example 12

Preparation of L-(2R,3R)-4-[(3-benzylcarbamoyl-2,3-dihydroxy-propionylamino)methyl]-benzoic acid

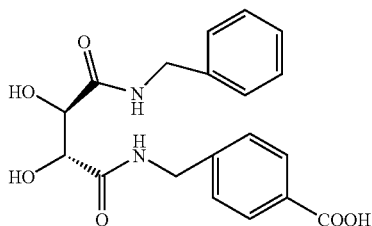

0.40 g (0.93 mmol) methyl L-(2R,3R)-4-[(3-benzylcarbamoyl-2,3-dihydroxy-propionylamino)methyl]-benzoate prepared in Example 8 was dissolved in 5 ml water/dioxane (volume ratio of 1:1) mixed solvent, and reacted according to the procedures of synthesizing compound (10), to obtain 0.05 g of a white solid, yield 7.7%, mp: 177-178° C., specific rotation $[\alpha]_D^{20}$=+106° (20 mg/2 ml, DMF). $^1$H-NMR (DMSO, 400 MHz), δ (ppm): 4.28-4.48 (6H, m, 2×CH$_2$ and 2×CH), 5.77 (2H, m, 2×OH), 7.22 (1H, m, ArH), 7.30 (4H, m, ArH), 7.41 (2H, d, J=8.16 Hz, ArH), 7.87 (2H, d, J=8.12 Hz, ArH), 8.71 (1H, t, J=6.48 Hz, CONH), 8.83 (1H, t, J=6.48 Hz, CONH), 12.81 (1H, br, COOH); FAB-MS m/e (%): 373.2 ([M+1]$^+$, 100), 318.4 (40), 274.4 (72).

Example 13

Preparation of methyl L-(2R,3R)-4-(3-benzylcarbamoyl-2,3-dihydroxy-propionylamino)-butyrate

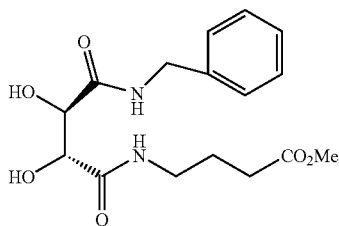

Step 1 Preparation of methyl L-(4R,5R)-4-(5-benzylaminocarbonyl-2,2-dimethyl-1,3-dioxolane-4-formyl)aminobutyrate According to the procedures in Step 4 of Example 8, 1.68 g (6.0 mmol) L-(4R,5R)-5-benzylaminocarbonyl-2,2-dimethyl-1,3-dioxolane-4-formic acid prepared in Example 8 and 0.90 g (6.0 mmol) methyl 14-aminobutyrate hydrochloride were reacted, to obtain 1.20 g of a colorless oily matter, yield 52.9%, specific rotation $[\alpha]_D^{20}$=−33.4° (20 mg/2 ml, CH$_3$OH). $^1$H-NMR (DMSO, 400 MHz), δ (ppm): 1.39 (6H, s, 2×CH$_3$), 1.69 (2H, m, CH$_2$), 2.31 (2H, t, J=7.56 Hz, CH$_2$), 3.12 (2H, m, CH$_2$), 3.58 (3H, s, CH$_3$), 4.32 (2H, d, J=6.16 Hz, CH$_2$), 4.51 (1H, d, J=6.16 Hz, CH), 4.54 (1H, d, J=6.16 Hz, CH), 7.22-7.34 (5H, m, ArH), 8.19 (1H, t, J=5.60 Hz, CONH), 8.81 (1H, t, J=5.88 Hz, CONH); EI-MS m/e (%): 378.1 (M$^+$, 35), 186(63), 176.1 (100), 91.1 (98).

Step 2 Preparation of methyl L-(2R,3R)-4-(3-benzylcarbamoyl-2,3-dihydroxy-propionylamino)-butyrate 1.20 g (3.17 mmol) methyl L-(4R,5R)-4-(5-benzylaminocarbonyl-2,2-dimethyl-1,3-dioxolane-4-formyl)aminobutyrate was dissolved in 10 ml methanol, and reacted according to the procedures of synthesizing compound (8), to obtain 0.40 g of a white solid, yield 37.3%, mp: 142-145° C., specific rotation $[\alpha]_D^{20}$=+84.8° (20 mg/2 ml, CH$_3$OH). $^1$H-NMR (DMSO, 400 MHz), δ (ppm): 1.69 (2H, m, CH$_2$), 2.31 (2H, t, J=7.00 Hz, CH$_2$), 3.13 (2H, m, CH$_2$), 3.58 (3H, s, CH$_3$), 4.27-4.39 (4H, m, CH$_2$ and 2×CH), 5.59 (2H, m, 2×OH), 7.22 (1H, m, ArH), 7.29 (4H, m, ArH), 7.78 (1H, t, J=6.20 Hz, CONH), 8.18 (1H, t, J=6.44 Hz, CONH), 12.81 (1H, br, COOH); EI-MS m/e (%): 338.1 (M$^+$, 10), 204.1 (84), 91.1 (100); HREI-MS Calcd. for C$_{16}$H$_{22}$N$_2$O$_6$: 338.1478. found: 338.1480.

Example 14

Preparation of L-(2R,3R)-4-(3-benzylcarbamoyl-2,3-dihydroxy-propionylamino)-butyric acid

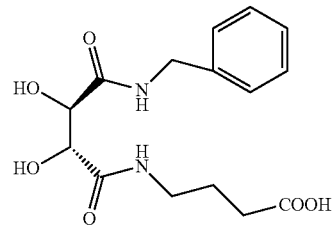

0.40 g (1.18 mmol) methyl L-(2R,3R)-4-(3-benzylcarbamoyl-2,3-dihydroxy-propionylamino)-butyrate prepared in Example 13 was dissolved in 5 ml water/dioxane (volume ratio of 1:1) mixed solvent, and reacted according to the procedures of synthesizing compound (10), to obtain 0.20 g of a white solid, yield 52.2%, mp: 169-170° C., specific rotation $[\alpha]_D^{20}$=+86.2° (20 mg/2 ml, CH$_3$OH). $^1$H-NMR (DMSO, 400 MHz), δ (ppm): 1.66 (2H, m, CH$_2$), 2.22 (2H, t, J=7.00 Hz, CH$_2$), 3.13 (2H, m, CH$_2$), 4.26-4.38 (4H, m, CH$_2$ and 2×CH), 5.57 (2H, m, 2×OH), 7.21 (1H, m, ArH), 7.29 (4H, m, ArH), 7.75 (1H, t, J=6.16 Hz, CONH), 8.18 (1H, t, J=6.96 Hz, CONH), 12.00 (1H, br, COOH); FAB-MS m/e (%): 325.2 ([M+1]$^+$, 100), 194.1 (18), 91.1 (47).

Example 15

Preparation of L-(2R,3R)-4-[(3-benzylcarbamoyl-2,3-dihydroxy-propionylamino)methyl]-cyclohexanecarboxylic acid

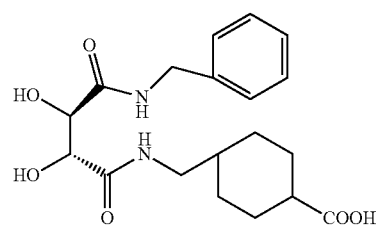

0.50 g (1.28 mmol) methyl L-(2R,3R)-4-(3-benzylcarbamoyl-2,3-dihydroxy-propionylaminomethyl)-cyclohexanecarboxylate prepared in Example 11 was dissolved in 5 ml water/dioxane (volume ratio of 1:1) mixed solvent, and reacted according to the procedures of synthesizing compound (10), to obtain 0.30 g of a white solid, yield 62.2%, mp: 236-238° C., specific rotation $[\alpha]_D^{20}$=+80.2° (20 mg/2 ml, $CH_3OH$). $^1$H-NMR (DMSO, 400 MHz), δ (ppm): 0.90 (2H, m, $CH_2$), 1.22 (2H, m, $CH_2$), 1.40 (1H, m, CH), 1.73 (2H, m, $CH_2$), 1.88 (2H, m, $CH_2$), 2.01 (1H, m, CH), 2.98 (2H, m, $CH_2$), 4.27-4.40 (4H, m, $CH_2$ and 2×CH), 5.60 (2H, m, 2×OH), 7.21 (1H, m, ArH), 7.28 (4H, m, ArH), 7.64 (1H, t, J=5.92 Hz, CONH), 8.20 (1H, t, J=6.44 Hz, CONH); 11.95 (1H, br, COOH); FAB-MS m/e (%): 379.2 ($[M+1]^+$, 100), 91.1 (17).

Example 16

Preparation of dimethyl L-(2R,3R)-5-(3-benzylcarbamoyl-2,3-dihydroxy-propionylamino)-isophthalate

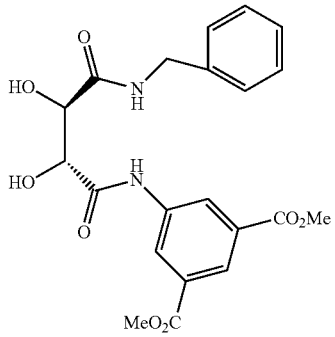

Step 1 Preparation of dimethyl L-(4R,5R)-5-[(5-benzylaminocarbonyl-2,2-dimethyl-1,3-dioxolane-4-formyl)amino]-isophthalate According to the procedures in Step 4 of Example 8, 2.80 g (10.0 mmol) L-(4R,5R)-5-benzylaminocarbonyl-2,2-dimethyl-1,3-dioxolane-4-formic acid prepared in Example 8 and 2.10 g (10.0 mmol) dimethyl 5-amino-isophthalate were reacted, to obtain 1.70 g of a white solid, mp: 146-147° C., yield 36.2%, specific rotation $[\alpha]_D^{20}$=−47.8° (20 mg/2 ml, $CH_3OH$). $^1$H-NMR (DMSO, 400 MHz), δ (ppm): 1.46 (6H, s, 2×$CH_2$), 4.35 (2H, d, J=6.16 Hz, $CH_2$), 4.72 (1H, d, J=6.44 Hz, CH), 4.76 (1H, d, J=6.44 Hz, CH), 7.22-7.35 (5H, m, ArH), 8.21 (1H, s, ArH), 8.59 (2H, s, ArH), 8.75 (1H, br, CONH), 10.68 (1H, s, CONH); EI-MS m/e (%): 470.2 (M', 65), 209.1 (51), 176.1 (98), 91.1 (100).

Step 2 Preparation of dimethyl L-(2R,3R)-5-(3-benzylcarbamoyl-2,3-dihydroxy-propionylamino)-isophthalate 1.10 g (2.34 mmol) dimethyl L-(4R,5R)-5-[(5-benzylaminocarbonyl-2,2-dimethyl-1,3-dioxolane-4-formyl)amino]-isophthalate was dissolved in 10 ml methanol, and reacted according to the procedures of synthesizing compound (8), to obtain 0.40 g of a white solid, yield 39.7%, specific rotation $[\alpha]_D^{20}$=+137.0° (20 mg/2 ml, $CH_3OH$). $^1$H-NMR (DMSO, 400 MHz), δ (ppm): 3.58 (6H, s, 2×$CH_3$), 4.27-4.50 (4H, m, $CH_2$ and 2×CH), 5.89 (1H, d, J=7.00 Hz, OH), 5.97 (1H, d, J=7.28 Hz, OH), 7.21 (1H, m, ArH), 7.30 (4H, m, ArH), 8.18 (1H, t, J=1.40 Hz, ArH), 8.33 (1H, t, J=6.32 Hz, CONH), 8.70 (2H, d, J=1.44 Hz, ArH), 10.29 (1H, s, CONH); EI-MS m/e (%): 430.0 ($M^+$, 15), 194.0 (49), 91.0 (100); HREI-MS Calcd. for $C_{21}H_{22}N_2O_8$: 430.1376. found: 430.1361.

Example 17

Preparation of methyl L-(2R,3R)-4-{[2,3-dihydroxy-3-(naphthyl-2-carbamoyl)-propionylamino]methyl}-benzoate

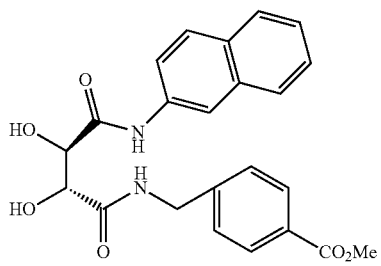

Step 1 Preparation of methyl L-(4R,5R)-4-(5-naphthyl-2-amino)carbonyl-2,2-dimethyl-1,3-dioxolane-4-formate According to the procedures in Step 2 of Example 8, 6.0 g (29.4 mmol) L-(4R,5R)-2,2-dimethyl-1,3-dioxolane-4,5-dicarboxylic monomethyl ester prepared in Example 8 and 5.03 g (35.2 mmol) 2-naphthylamine were reacted, to obtain 8.5 g of an oily matter, exhibiting a single spot by TLC, without further purification, yield 87.9%.

Step 2 Preparation of L-(4R,5R)-4-(5-naphthyl-2-amino)carbonyl-2,2-dimethyl-1,3-dioxolane-4-formic acid 8.09 g (24.6 mmol) methyl L-(4R,5R)-4-(5-naphthyl-2-amino)carbonyl-2,2-dimethyl-1,3-dioxolane-4-formate was dissolved in 300 ml water/dioxane (volume ratio of 1:1) mixed solvent, and reacted according to the procedures in Step 3 of Example 8, to obtain 6.0 g of a yellowish solid, yield 77.4%, mp: 168-169° C., specific rotation $[\alpha]_D^{20}$=−44.1° (20 mg/2 ml, $CH_3OH$). $^1$H-NMR (DMSO, 400 MHz), δ (ppm): 1.45 (3H, s, $CH_3$), 1.46 (3H, s, $CH_3$), 4.80 (1H, d, J=5.88 Hz, CH), 4.84 (1H, d, J=5.88 Hz, CH), 7.42 (1H, t, J=6.72 Hz, ArH), 7.49 (1H, t, J=6.72 Hz, ArH), 7.66 (2H, m, ArH), 7.83-7.90 (3H, m, ArH), 8.35 (1H, s, ArH), 10.40 (1H, br, CONH), 13.25 (1H, br, COOH); FAB-MS m/e (%): 316.2 ($[M+1]^+$, 100), 143.2 (19).

Step 3 Preparation of methyl L-(4R,5R)-4-{[(5-naphthyl-2-aminocarbonyl-2,2-dimethyl-1,3-dioxolane-4-formyl)amino]-methyl}benzoate 1.28 g (4.0 mmol) L-(4R,5R)-4-(5-naphthyl-2-amino)carbonyl-2,2-dimethyl-1,3-dioxolane-4-formic acid and 0.80 g (2.0 mmol) methyl (4-aminomethyl)benzoate were reacted according to the procedures in Step 4 of Example 8, to obtain 1.24 g of a colorless oily matter, yield 67.1%, specific rotation $[\alpha]_D^{20}$=−58.9° (20 mg/2 ml, DMF). $^1$H-NMR (DMSO, 400 MHz), δ (ppm): 1.47 (3H, s, $CH_3$), 1.49 (3H, s, $CH_3$), 3.83 (3H, s, $CH_3$), 4.42 (2H, m, $CH_2$), 4.75 (1H, d, J=6.20 Hz, CH), 4.81 (1H, d, J=6.44 Hz, CH), 7.41-7.49 (4H, m, ArH), 7.68

(1H, m, ArH); 7.66 (1H, m, ArH), 7.83-7.92 (5H, m, ArH), 8.35 (1H, s, ArH), 8.89 (1H, t, J=6.16 Hz, CONH), 10.45 (1H, br, CONH); HREI-MS Calcd. for $C_{26}H_{26}N_2O_6$: 462.1791. found: 462.1788.

Step 4 Preparation of methyl L-(2R,3R)-4-{[2,3-dihydroxy-3-(naphthalen-2-ylcarbamoyl)-propionylamino]methyl}-benzoate 1.10 g (2.38 mmol) methyl L-(4R,5R)-4-{[(5-naphthyl-2-aminocarbonyl-2,2-dimethyl-1,3-dioxolane-4-formyl)amino]-methyl}benzoate was dissolved in 10 ml methanol, and reacted according to the procedures of synthesizing compound (8), to obtain 0.80 g of a white solid, yield 79.6%, specific rotation $[\alpha]_D^{20}$=+174.0° (20 mg/2 ml, $CH_3OH$). $^1$H-NMR (DMSO, 400 MHz), δ (ppm): 3.85 (3H, s, $CH_3$), 4.38 (1H, d, J=15.68 Hz, CH), 4.53 (1H, d, J=1.68 Hz, ×$CH_2$), 4.52 (2H, m, CH and ½×$CH_2$), 6.02 (2H, br, 2×OH), 7.40-7.49 (4H, m, ArH), 7.69-7.91 (6H, m, ArH), 8.45 (1H, t, J=1.40 Hz, ArH), 8.8.47 (1H, br, CONH), 9.86 (1H, br, CONH); ELMS m/e (%): 422.0 ($M^+$, 45), 143.2 (100); HREI-MS Calcd. for $C_{23}H_{22}N_2O_6$: 422.1480. found: 422.1480.

Example 18

Preparation of methyl L-(2R,3R)-4-{[2,3-dihydroxy-3-(naphthyl-2-carbamoyl)-propionylamino]methyl}-cyclohexanecarboxylate

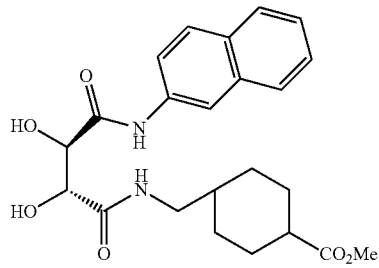

Step 1 Preparation of methyl L-(4R,5R)-4-{[(5-naphthyl-2-aminocarbonyl-2,2-dimethyl-1,3-dioxolane-4-formyl)amino]-methyl}cyclohexanecarboxylate 0.64 g (2.0 mmol) L-(4R,5R)-4-(5-naphthyl-2-amino)carbonyl-2,2-dimethyl-1,3-dioxolane-4-formic acid prepared in Example 17 and 0.41 g (2.0 mmol) methyl (4-aminomethyl)cyclohexanecarboxylate hydrochloride were reacted according to the procedures in Step 4 of Example 8, to obtain 0.70 g of a white solid, mp: 130-131° C., yield 74.8%, specific rotation $[\alpha]_D^{20}$=−61.6° (20 mg/2 ml, DMF). $^1$H-NMR (DMSO, 400 MHz), δ (ppm): 0.93 (2H, m, $CH_2$), 1.28 (2H, m, $CH_2$), 1.40 (7H, m, 2×$CH_3$ and ½×$CH_2$), 1.71 (2H, d, J=12.36 Hz, $CH_2$), 1.87 (2H, d, J=11.48 Hz, $CH_2$), 2.22 (1H, m, ×$CH_2$), 2.99 (2H, t, J=6.44 Hz, $CH_2$), 3.57 (3H, s, $CH_3$), 4.70 (2H, d, J=6.72 Hz, 2×CH), 7.43 (1H, t, J=6.72 Hz, ArH), 7.49 (1H, t, J=8.16 Hz, ArH), 7.66 (2H, m, ArH), 7.83-7.89 (3H, m, ArH), 8.17 (1H, br, CONH), 8.34 (1H, s, ArH), 10.39 (1H, br, CONH); HREI-MS Calcd. for $C_{26}H_{32}N_2O_6$: 468.2260. found: 468.2261.

Step 2 Preparation of methyl L-(2R,3R)-4-{[2,3-dihydroxy-3-(naphthalen-2-ylcarbamoyl)-propionylamino]methyl}-cyclohexanecarboxylate 0.50 g (1.07 mmol) methyl L-(4R,5R)-4-{[(5-naphthyl-2-aminocarbonyl-2,2-dimethyl-1,3-dioxolane-4-formyl)amino]-methyl}cyclohexanecarboxylate was dissolved in 10 ml methanol, and reacted according to the procedures of synthesizing compound (8), to obtain 0.22 g of a white solid, yield 48.1%. $^1$H-NMR (DMSO, 400 MHz), δ (ppm): 0.93 (2H, m, $CH_2$), 1.27 (2H, m, $CH_2$), 1.46 (1H, m, CH), 1.74 (2H, m, $CH_2$), 1.98 (2H, m, $CH_2$), 2.23 (1H, m, CH), 2.97 (2H, m, $CH_2$), 3.57 (3H, s, $CH_3$), 4.34 (1H, d, J=5.32 Hz, CH), 4.45 (1H, d, J=7.00 Hz, CH), 5.78 (1H, d, J=7.00 Hz, OH), 5.95 (1H, d, J=7.00 Hz, OH), 7.41 (1H, t, J=6.76 Hz, ArH), 7.47 (1H, t, J=7.00 Hz, ArH), 7.72-7.87 (5H, m, ArH), 8.44 (1H, s, CONH), 9.80 (1H, s, CONH); EI-MS m/e (%): 428.2 ($M^+$, 60), 258.1 (30), 143.1 (100); HREI-MS Calcd. for $C_{23}H_{28}N_2O_6$: 428.1947. found: 428.1947.

Example 19

Preparation of methyl L-(2R,3R)-2-[2,3-dihydroxy-3-(naphthalen-2-ylcarbamoyl)-propionylamino]-3-phenyl-propionate

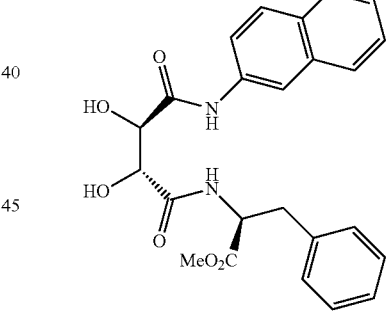

0.45 g (0.87 mmol) methyl L-(2R,3R)-2-[2,3-diacetoxy-3-(naphthalen-2-ylcarbamoyl)-propionylamino]-3-phenyl-propionate prepared in Example 1, and 0.05 g (0.92 mmol) sodium methoxide were dissolved in 10 ml methanol, reacted at room temperature with stirring for 12 hours, and filtered; the resulting mother liquor was evaporated to dryness under reduced pressure to obtain an oily matter, which was loaded on a silica gel chromatographic column, and eluted with cyclohexane:ethyl acetate=3:1, to obtain 0.28 g of an oily matter, yield 41.4%, yield 74.7%, specific rotation $[\alpha]_D^{20}$=+129.5° (20 mg/2 ml, DMF). $^1$H-NMR (DMSO, 400 MHz), δ (ppm): 3.08 (2H, m, $CH_2$), 3.63 (3H, s, $CH_3$), 4.35 (1H, d, J=7.28 Hz, CH), 4.45 (1H, d, J=7.28 Hz, CH), 4.63 (1H, q, J=7.28 Hz, CH), 5.89 (1H, d, J=7.00 Hz, OH), 5.96 (1H, d, J=7.00 Hz, OH), 7.18-7.28 (5H, m, ArH), 7.40 (1H, t, J=7.00 Hz, ArH), 7.45 (1H, t, J=7.00 Hz, ArH), 7.78-7.93 (5H, m, ArH), 8.42 (1H, s, CONH), 9.77 (1H, s, CONH); HREI-MS Calcd. for $C_{24}H_{24}N_2O_6$: 436.1637. found: 436.1637.

Example 20

Preparation of ethyl L-(2R,3R)-2-[2,3-dihydroxy-3-(4-phenoxy-phenylcarbamoyl)-propionylamino]-3-phenyl-propionate

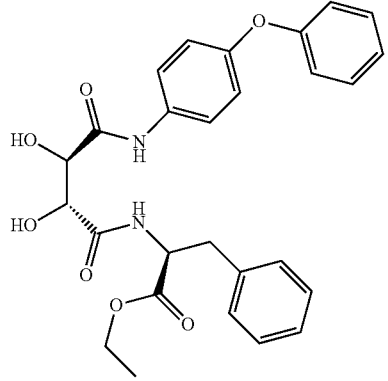

Step 1 Preparation of methyl L-(2R,3R)-2-[2,3-diacetoxy-3-(4-phenoxy-phenylcarbamoyl)-propionylamino]-3-phenyl-propionate 2.00 g (5.00 mmol) L-(2R,3R)-2,3-diacetoxy-3-(4-phenoxy-phenylcarbamoyl)propionic acid prepared in Example 2 and 1.08 g (5.00 mmol) methyl L-phenprobamate hydrochloride were reacted according to the procedures of synthesizing compound (1), to obtain 1.20 g of a white solid, exhibiting a single spot by TLC, without further purification, yield 42.7%.

Step 2 Preparation of ethyl L-(2R,3R)-2-[2,3-dihydroxy-3-(4-phenoxy-phenylcarbamoyl)-propionylamino]-3-phenyl-propionate 0.45 g (0.80 mmol) methyl L-(2R,3R)-2-[2,3-diacetoxy-3-(4-phenoxy-phenylcarbamoyl)-propionylamino]-3-phenyl-propionate, 0.05 g (0.92 mmol) sodium methoxide were dissolved in 10 ml ethanol, and reacted according to the procedures of synthesizing compound (19), to obtain 0.24 g of a white solid, yield 61.0%, specific rotation $[\alpha]_D^{20}$=+113.0° (20 mg/2 ml, $CH_3OH$). $^1$H-NMR (DMSO, 400 MHz), δ (ppm): 1.14 (3H, t, J=7.00 Hz, $CH_3$), 3.06 (2H, d, J=6.72 Hz, $CH_2$), 4.07 (2H, q, J=7.28 Hz, $CH_2$), 4.31 (1H, d, J=7.00 Hz, CH), 4.40 (1H, d, J=7.00 Hz, CH), 4.59 (1H, m, CH), 5.81 (1H, d, J=7.04 Hz, OH), 5.92 (1H, d, J=7.32 Hz, OH), 6.97 (4H, m, ArH), 7.10 (1H, t, J=7.28 Hz, ArH), 7.17-7.30 (5H, m, ArH), 7.36 (2H, m, ArH), 7.74 (2H, d, J=6.72 Hz, ArH), 7.87 (1H, t, J=8.12 Hz, CONH), 9.65 (1H, s, CONH); HREI-MS Calcd. for $C_{27}H_{28}N_2O_7$: 492.1897. found: 492.1901.

Example 21

Preparation of methyl L-(2R,3R)-4-{[2,3-dihydroxy-3-(4-phenoxy-phenylcarbamoyl)-propionylamino]methyl}-benzoate

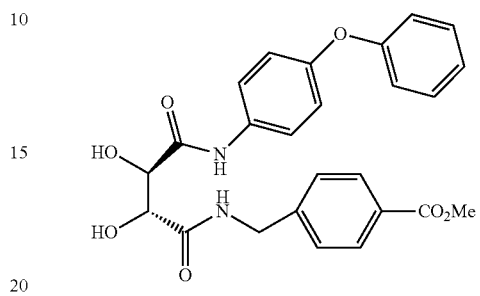

0.50 g (0.91 mmol) methyl L-(2R,3R)-4-{[2,3-diacetoxy-3-(4-phenoxy-phenylcarbamoyl)-propionylamino]methyl}-benzoate prepared in Example 2, 0.05 g (0.92 mmol) sodium methoxide were dissolved in 10 ml methanol, and reacted according to the procedures of synthesizing compound (19), to obtain 0.25 g of a white solid, yield 59.2%, specific rotation $[\alpha]_D^{20}$=+138.0° (20 mg/2 ml, DMSO). $^1$H-NMR (DMSO, 400 MHz), δ (ppm): 3.84 (3H, s, $CH_3$), 4.39 (2H, m, CH and ½×$CH_2$), 4.47 (2H, m, CH and ½×$CH_2$), 5.87 (1H, d, J=7.00 Hz, OH), 5.97 (1H, d, J=7.00 Hz, OH), 6.97 (4H, m, ArH), 7.11 (1H, t, J=7.28 Hz, ArH), 7.36 (2H, t, J=7.56 Hz, ArH), 7.44 (2H, d, J=8.40 Hz, ArH), 7.78 (2H, d, J=7.00 Hz, ArH), 7.90 (2H, d, J=8.48 Hz, ArH), 8.47 (1H, t, J=6.44 Hz, CONH), 9.71 (1H, s, CONH); HREI-MS Calcd. for $C_{25}H_{24}N_2O_7$: 464.1584. found: 464.1590.

Example 22

Preparation of methyl L-(2R,3R)-4-[2,3-dihydroxy-3-(4-phenoxy-phenylcarbamoyl)-propionylamino]-butyrate

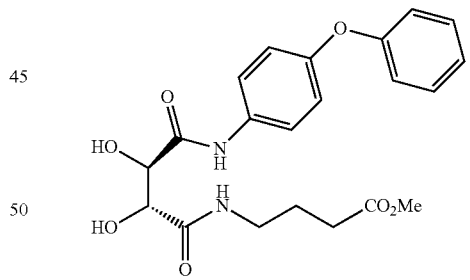

0.64 g (1.30 mmol) methyl L-(2R,3R)-4-[2,3-diacetoxy-3-(4-phenoxy-phenylcarbamoyl)-propionylamino]-butyrate prepared in Example 3, 0.05 g (0.92 mmol) sodium methoxide were dissolved in 10 ml methanol, and reacted according to the procedures of synthesizing compound (19), to obtain 0.33 g of a white solid, yield 61.0%, specific rotation $[\alpha]_D^{20}$=+120.0° (20 mg/2 ml, DMSO). $^1$H-NMR (DMSO, 400 MHz), δ (ppm): 1.69 (2H, m, $CH_2$), 2.32 (2H, m, $CH_2$), 3.18 (2H, m, $CH_2$), 3.58 (3H, s, $CH_3$), 4.30 (1H, d, J=7.00 Hz, CH), 4.40 (1H, d, J=7.00 Hz, CH), 5.69 (1H, d, J=7.00 Hz, OH), 5.84 (1H, d, J=7.00 Hz, OH), 6.97 (4H, m, ArH), 7.10 (1H, t, J=7.28 Hz, ArH), 7.36 (2H, t, J=7.56 Hz, ArH), 7.75 (2H, d, J=8.96 Hz, ArH), 7.83 (1H, t, J=6.16 Hz, CONH), 9.65 (1H, s, CONH); HREI-MS Calcd. for $C_{21}H_{24}N_2O_7$: 416.1584. found: 416.1589.

Example 23

Preparation of methyl L-(2R,3R)-4-[2,3-dihydroxy-3-(naphthalen-2-ylcarbamoyl)-propionylamino]-butyrate

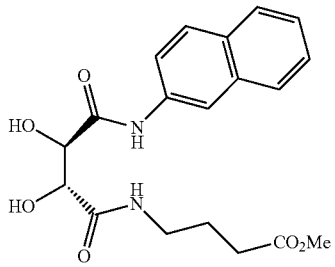

Step 1 Preparation of methyl L-(2R,3R)-4-[2,3-diacetoxy-3-(naphthalen-2-ylcarbamoyl)-propionylamino]-butyrate 1.80 g (5.00 mmol) L-(2R,3R)-2,3-diacetoxy-3-(naphthalen-2-ylcarbamoyl)-propionic acid prepared in Example 1 and 0.77 g (5.00 mmol) methyl 4-aminobutyrate hydrochloride were reacted according to the procedures of synthesizing compound (1), to obtain 0.45 g of a white solid, exhibiting a single spot by TLC, without further purification, yield 19.6%.

Step 2 Preparation of methyl L-(2R,3R)-4-[2,3-dihydroxy-3-(naphthalen-2-ylcarbamoyl)-propionylamino]-butyrate 0.45 g (1.00 mmol) methyl L-(2R,3R)-4-[2,3-diacetoxy-3-(naphthalen-2-ylcarbamoyl)-propionylamino]-butyrate, 0.05 g (0.92 mmol) sodium methoxide were dissolved in 10 ml methanol, and reacted according to the procedures of synthesizing compound (19), to obtain 0.23 g of a white solid, yield 61.2%, specific rotation $[\alpha]_D^{20}=+157.0°$ (20 mg/2 ml, DMSO). $^1$H-NMR (DMSO, 400 MHz), δ (ppm): 1.70 (2H, t, J=7.32 Hz, CH$_2$), 1.70 (2H, t, J=7.32 Hz, CH$_2$), 2.32 (2H, m, CH$_2$), 3.19 (2H, m, CH$_2$), 3.19 (3H, s, CH$_3$), 4.33 (1H, d, J=7.28 Hz, CH), 4.46 (1H, d, J=7.28 Hz, CH), 5.75 (1H, d, J=7.00 Hz, OH), 5.92 (1H, d, J=7.04 Hz, OH), 7.41 (1H, t, J=8.12 Hz, ArH), 7.47 (1H, t, J=7.00 Hz, ArH), 7.75-7.7.87 (5H, m, ArH), 8.43 (1H, s, CONH), 9.77 (1H, s, CONH); HREI-MS Calcd. for C$_{19}$H$_{22}$N$_2$O$_6$: 374.1478. found: 374.1461.

Example 24

Preparation of ethyl L-(2R,3R)-2-[3-(3-di-n-propylaminoformyl-phenylcarbamoyl)-2,3-dihydroxy-propionylamino]-3-phenyl-propionate

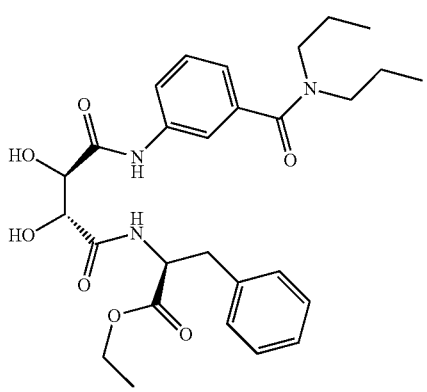

Step 1 Preparation of methyl L-(2R,3R)-2-[3-(3-di-n-propylaminoformyl-phenylcarbamoyl)-2,3-diacetoxy-propionylamino]-3-phenyl-propionate 1.50 g (3.44 mmol) L-(2R,3R)-2,3-diacetoxy-3-(3-di-n-propylaminoformyl-phenylcarbamoyl)propionic acid prepared in Example 4 and 0.74 g (3.44 mmol) methyl L-phenprobamate hydrochloride were reacted according to the procedures of synthesizing compound (1), to obtain 2.00 g of an oily matter, exhibiting a single spot by TLC, without further purification, yield 97.4%.

Step 2 Preparation of ethyl L-(2R,3R)-2-[3-(3-di-n-propylaminoformyl-phenylcarbamoyl)-2,3-dihydroxy-propionylamino]-3-phenyl-propionate 0.90 g (1.54 mmol) methyl L-(2R,3R)-2-[3-(3-di-n-propylaminoformyl-phenylcarbamoyl)-2,3-diacetoxy-propionylamino]-3-phenyl-propionate, 0.05 g (0.92 mmol) sodium methoxide were dissolved in 10 ml ethanol, and reacted according to the procedures of synthesizing compound (19), to obtain 0.22 g of a white solid, yield 27.1%. $^1$H-NMR (DMSO, 400 MHz), δ (ppm): 0.67 (3H, m, CH$_3$), 0.91 (3H, m, CH$_3$), 1.15 (3H, t, J=7.28 Hz, CH$_3$), 1.48 (2H, m, CH$_2$), 1.61 (2H, m, CH$_2$), 3.06 (2H, d, J=6.44 Hz, CH$_2$), 3.07 (2H, m, CH$_2$), 3.37 (2H, m, CH$_2$), 4.07 (2H, q, J=7.00 Hz, CH$_2$), 4.34 (1H, d, J=1.68 Hz, CH), 4.41 (1H, d, J=1.68 Hz, CH), 5.92 (2H, br, 2×OH), 7.03 (1H, d, J=7.56 Hz, ArH), 7.17-7.30 (5H, m, ArH), 7.39 (1H, t, J=7.84 Hz, ArH), 7.68 (1H, d, J=8.12 Hz, ArH), 7.76 (1H, s, ArH), 7.85 (1H, d, J=7.88 Hz, CONH), 9.72 (1H, s, CONH); HREI-MS Calcd. for C$_{28}$H$_{37}$N$_3$O$_7$: 527.2632. found: 527.2633.

Example 25

Preparation of benzyl L-(2R,3R)-4-(3-benzylcarbamoyl-2,3-dihydroxy-propionylamino)-butyrate

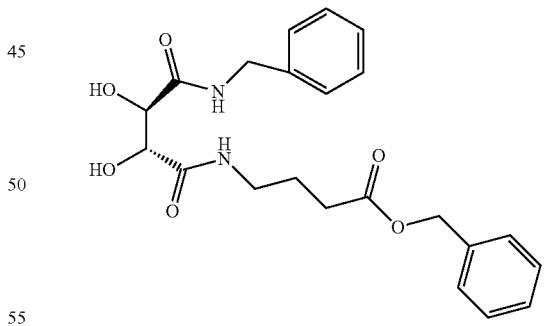

Step 1 Preparation of methyl L-(2R,3R)-4-(3-benzylcarbamoyl-2,3-diacetoxy-propionylamino)-butyrate 1.24 g (3.83 mmol) L-(2R,3R)-2,3-diacetoxy-3-(benzylcarbamoyl)propionic acid prepared in Example 7 and 0.98 g (3.83 mmol) 4-benzylpiperazine were reacted according to the procedures of synthesizing compound (1), to obtain 0.60 g of an oily matter, exhibiting a single spot by TLC, without further purification, yield 60.5%.

Step 2 Preparation of benzyl L-(2R,3R)-4-(3-benzyl-carbamoyl-2,3-dihydroxy-propionylamino)-butyrate 0.42 g (1.00 mmol) methyl L-(2R,3R)-4-(3-benzylcarbamoyl-2,3-diacetoxy-propionylamino)-butyrate, 0.05 g (0.92 mmol) sodium methoxide were dissolved in 10 ml benzyl alcohol, and reacted according to the procedures of synthesizing compound (19), to obtain 0.10 g of a white solid, yield 61.2%, specific rotation $[\alpha]_D^{20}$=+60.9° (20 mg/2 ml, DMF). Or, they were reacted according to the procedures of synthesizing compound (8), to obtain 0.40 g of a white solid, yield 39.7%, specific rotation $[\alpha]_D^{20}$=+137.0° (20 mg/2 ml, $CH_3OH$). $^1$H-NMR (DMSO, 400 MHz), δ (ppm): 1.71 (2H, m, $CH_2$), 2.37 (2H, t, J=7.00 Hz, $CH_2$), 3.15 (2H, m, $CH_2$), 4.25-4.40 (4H, m, $CH_2$ and 2×CH), 5.08 (2H, s, $CH_2$), 5.58 (1H, d, J=7.28 Hz, OH), 5.61 (1H, d, J=7.00 Hz, OH), 7.21-37 (10H, m, ArH), 7.80 (1H, t, J=6.16 Hz, CONH), 8.19 (2H, d, J=6.44 Hz, CONH); HREI-MS Calcd. for $C_{22}H_{26}N_2O_6$: 414.1791. found: 414.1785.

Example 26

Preparation of ethyl L-(2R,3R)-4-[2,3-dihydroxy-3-(4-phenoxy-phenylcarbamoyl)-propionylamino]-cyclohexanecarboxylate

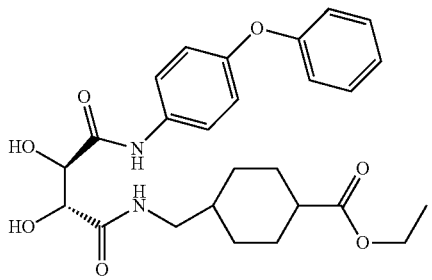

Step 1 Preparation of methyl L-(2R,3R)-4-[2,3-diacetoxy-3-(4-phenoxy-phenylcarbamoyl)-propionylamino]-cyclohexanecarboxylate 2.00 g (5.00 mmol) L-(2R,3R)-2,3-diacetoxy-3-(4-phenoxy-phenylcarbamoyl)propionic acid prepared in Example 2 and 1.01 g (5.00 mmol) methyl 4-aminomethylbenzoate hydrochloride were reacted according to the procedures of synthesizing compound (1), to obtain 1.67 g of an oily matter, exhibiting a single spot by TLC, without further purification, yield 60.3%.

Step 2 Preparation of ethyl L-(2R,3R)-4-[2,3-dihydroxy-3-(4-phenoxy-phenylcarbamoyl)-propionylamino]-cyclohexanecarboxylate 0.45 g (0.81 mmol) methyl L-(2R,3R)-4-[2,3-diacetoxy-3-(4-phenoxy-phenylcarbamoyl)-propionylamino]-cyclohexanecarboxylate, 0.05 g (0.92 mmol) sodium methoxide were dissolved in 10 ml ethanol, and reacted according to the procedures of synthesizing compound (19), to obtain 0.28 g of a white solid, yield 71.2%. $^1$H-NMR (DMSO, 400 MHz), δ (ppm): 0.93 (2H, m, $CH_2$), 1.15 (3H, t, J=7.28 Hz, $CH_3$), 1.31 (2H, m, $CH_2$), 1.44 (1H, m, CH), 1.75 (2H, m, $CH_2$), 1.87 (2H, m, $CH_2$), 2.20 (1H, m, CH), 2.99 (2H, m, $CH_2$), 4.04 (2H, q, J=7.28 Hz, $CH_2$), 4.31 (1H, d, J=7.00 Hz, CH), 4.40 (1H, d, J=7.28 Hz, CH), 5.71 (1H, d, J=7.00 Hz, OH), 5.84 (1H, d, J=7.28 Hz, OH), 6.97 (4H, m, ArH), 7.10 (1H, t, J=7.60 Hz, ArH), 7.36 (2H, t, J=7.60 Hz, ArH), 7.70 (1H, t, J=6.16 Hz, CONH), 7.77 (2H, d, J=7.00 Hz, ArH), 9.65 (1H, s, CONH); HREI-MS Calcd. for $C_{26}H_{32}N_2O_7$: 484.2210. found: 484.2213.

Example 27

Preparation of dimethyl L-(2R,3R)-5-[2,3-dihydroxy-3-(1-methoxycarbonyl-2-phenyl-ethylcarbamoyl)-propionylamino]-isophthalate

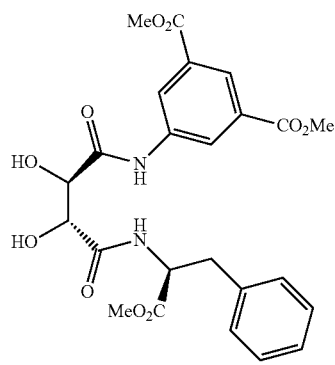

0.72 g (1.23 mmol) dimethyl L-(2R,3R)-5-[2,3-diacetoxy-3-(1-methoxycarbonyl-2-phenyl-ethylcarbamoyl)-propionylamino]-isophthalate prepared in Example 5, 0.05 g (0.92 mmol) sodium methoxide were dissolved in 10 ml methanol, and reacted according to the procedures of synthesizing compound (19), to obtain 0.34 g of a white solid, yield 55.1%. $^1$H-NMR ($CDCl_3$, 400 MHz), δ (ppm): 3.07 (2H, m, $CH_2$), 3.63 (3H, s, $CH_3$), 3.89 (6H, s, 2×$CH_3$), 4.33 (1H, m, CH), 4.43 (1H, m, CH), 4.63 (1H, q, J=7.28 Hz, CH), 5.81 (1H, br, OH), 5.95 (1H, br, OH), 7.17-7.28 (5H, m, ArH), 7.92 (1H, d, J=8.16 Hz, CONH), 8.19 (1H, d, J=1.40 Hz, ArH), 8.67 (1H, d, J=1.40 Hz, ArH), 10.22 (1H, s, CONH); HREI-MS Calcd. for $C_{28}H_{30}N_2O_{12}$: 586.1799. found: 586.1777.

Example 28

Preparation of methyl L-(2R,3R)-4-{[3-(3-di-n-propylaminoformyl-phenylcarbamoyl)-2,3-dihydroxy-propionylamino]methyl}benzoate

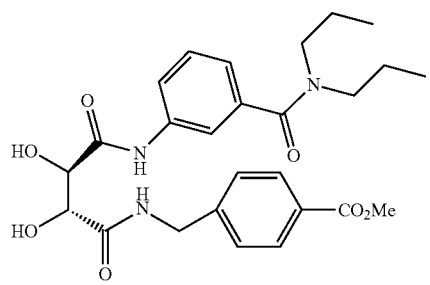

0.50 g (0.86 mmol) methyl L-(2R,3R)-4-{[3-(3-di-n-propylaminoformyl-phenylcarbamoyl)-2,3-diacetoxy-propionylamino]methyl}-benzoate prepared in Example 4, and 0.05 g (0.92 mmol) sodium methoxide were dissolved in 10 ml methanol, and reacted according to the procedures of synthesizing compound (19), to obtain 0.15 g of a white solid, yield 35.1%. $^1$H-NMR (DMSO, 400 MHz), δ (ppm): 0.67 (3H, m, CH$_3$), 0.91 (3H, m, CH$_3$), 1.48 (2H, m, CH$_2$), 1.58 (2H, m, CH$_2$), 3.12 (2H, m, CH$_2$), 3.34 (2H, m, CH$_2$), 3.85 (3H, m, CH$_3$), 4.34-4.49 (4H, m, 2×CH and CH$_2$), 5.87 (1H, br, OH), 5.97 (1H, br, OH), 6.99 (1H, d, J=7.56 Hz, ArH), 7.36 (1H, t, J=7.84 Hz, ArH), 7.45 (2H, d, J=8.40 Hz, ArH), 7.74 (1H, d, J=8.40 Hz, ArH), 7.82 (1H, s, ArH), 7.89 (2H, d, J=8.40 Hz, ArH), 8.45 (1H, t, J=6.44 Hz, CONH), 9.81 (1H, s, CONH); FAB-MS m/e (%): 500.1 ([M+1]$^+$, 100).

Example 29

Preparation of L-(2R,3R)-4-[4-(3-chlorophenyl)-piperazin-1-yl]-2,3-dihydroxy-N-naphthalen-2-yl-4-oxo-butyramide

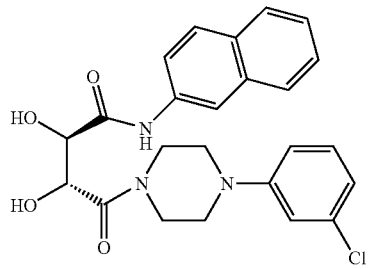

Step 1 Preparation of L-(2R,3R)-4-[4-(3-chlorophenyl)-piperazin-1-yl]-2,3-diacetoxy-N-naphthalen-2-yl-4-oxo-butyramide 2.00 g (5.57 mmol) L-(2R,3R)-2,3-diacetoxy-3-(naphthalen-2-ylcarbamoyl)-propionic acid prepared in Example 1 and 1.10 g (5.57 mmol) N-3-chlorophenylpiperazine were reacted according to the procedures of synthesizing compound (1), to obtain 1.00 g of an oily matter, exhibiting a single spot by TLC, without further purification, yield 33.4%.

Step 2 Preparation of L-(2R,3R)-4-[4-(3-chlorophenyl)-piperazin-1-yl]-2,3-dihydroxy-N-naphthalen-2-yl-4-oxo-butyramide 0.60 g (1.12 mmol) L-(2R,3R)-4-[4-(3-chlorophenyl)-piperazin-1-yl]-2,3-diacetoxy-N-naphthalen-2-yl-4-oxo-butyramide, 0.05 g (0.92 mmol) sodium methoxide were dissolved in 10 ml methanol, and reacted according to the procedures of synthesizing compound (19), to obtain 0.30 g of a white solid, yield 59.3%, specific rotation [α]$_D^{20}$=+26.5° (20 mg/2 ml, DMF). $^1$H-NMR (DMSO, 400 MHz), δ (ppm): 3.23 (4H, m, 2×CH$_2$), 3.76 (4H, m, 2×CH$_2$), 4.35 (1H, s, CH), 4.81 (1H, d, J=4.48 Hz, CH), 5.17 (1H, d, J=7.32 Hz, OH), 6.02 (1H, d, J=6.16 Hz, OH), 6.82 (1H, d, J=7.84 Hz, ArH), 6.93 (1H, d, J=8.40 Hz, ArH), 6.99 (1H, s, ArH), 7.23 (1H, t, J=8.12 Hz, ArH), 7.41 (1H, t, J=7.00 Hz, ArH), 7.47 (1H, t, J=7.00 Hz, ArH), 7.30-7.89 (4H, m, ArH), 8.39 (1H, s, ArH), 9.85 (1H, s, CONH); HREI-MS Calcd. for C$_{24}$H$_{24}$N$_3$O$_4$Cl: 453.1455. found: 453.1449.

Example 30

Preparation of L-(2R,3R)-3-{4-[4-(3-chlorophenyl)-piperazin-1-yl]-2,3-dihydroxy-4-oxo-butyrylamino}-N,N-di-n-propyl-benzamide

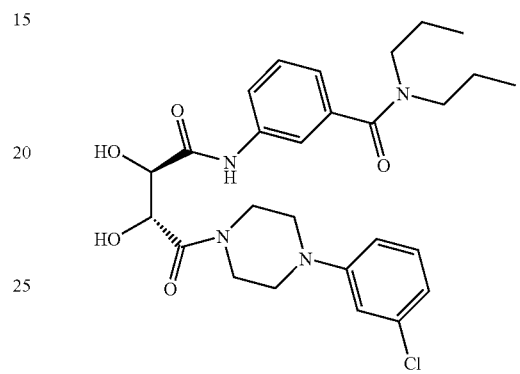

Step 1 Preparation of L-(2R,3R)-3-{4-[4-(3-chlorophenyl)-piperazin-1-yl]-2,3-diacetoxy-4-oxo-butyrylamino}-N,N-di-n-propyl-benzamide 2.37 g (5.57 mmol) L-(2R,3R)-2,3-diacetoxy-3-(3-di-n-propylaminoformyl-phenylcarbamoyl)propionic acid prepared in Example 4 and 1.10 g (5.57 mmol) 3-chlorophenylpiperazine were reacted according to the procedures of synthesizing compound (1), to obtain 1.00 g of an oily matter, exhibiting a single spot by TLC, without further purification, yield 29.7%.

Step 2 Preparation of L-(2R,3R)-3-{4-[4-(3-chlorophenyl)-piperazin-1-yl]-2,3-dihydroxy-4-oxo-butyrylamino}-N,N-di-n-propyl-benzamide 0.32 g (0.52 mmol) L-(2R,3R)-3-{4-[4-(3-chlorophenyl)-piperazin-1-yl]-2,3-diacetoxy-4-oxo-butyrylamino}-N,N-di-n-propyl-benzamide, 0.02 g (0.34 mmol) sodium methoxide were dissolved in 5 ml methanol, and reacted according to the procedures of synthesizing compound (19), to obtain 0.08 g of a white solid, yield 28.9%. $^1$H-NMR (DMSO, 400 MHz), δ (ppm): 0.67 (3H, t, J=6.16 Hz, CH$_3$), 0.91 (3H, t, J=6.48 Hz, CH$_3$), 1.46 (2H, q, J=6.16 Hz, CH$_2$), 1.60 (2H, q, J=6.44 Hz, CH$_2$), 3.12 (2H, m, CH$_2$), 3.22 (4H, m, 2×CH$_2$), 3.36 (2H, m, CH$_2$), 3.76 (4H, m, 2×CH$_2$), 4.28 (1H, m, CH), 4.77 (1H, m, CH), 5.11 (1H, d, J=7.56 Hz, OH), 5.96 (1H, d, J=6.72 Hz, OH), 6.80 (1H, d, J=8.40 Hz, ArH), 6.92 (1H, d, J=8.12 Hz, ArH), 7.00 (2H, m, ArH), 7.23 (1H, t, J=7.84 Hz, ArH), 7.36 (1H, t, J=7.88 Hz, ArH), 7.73 (1H, d, J=8.44 Hz, ArH), 7.78

(1H, s, ArH), 9.81 (1H, s, CONH); HREI-MS Calcd. for $C_{27}H_{35}N_4O_5Cl$: 530.2296. found: 530.2295.

Example 31

Preparation of dimethyl L-(2R,3R)-5-[2,3-dihydroxy-3-(4-methoxycarbonyl-benzylcarbamoyl)-propionylamino]-isophthalate

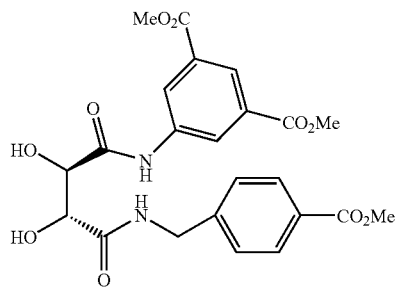

0.34 g (0.59 mmol) dimethyl L-(2R,3R)-5-[2,3-diacetoxy-3-(4-methoxycarbonyl-benzylcarbamoyl)-propionylamino]-isophthalate prepared in Example 6, 0.02 g (0.34 mmol) sodium methoxide were dissolved in 5 ml methanol, and reacted according to the procedures of synthesizing compound (19), to obtain 0.16 g of a white solid, yield 55.2%. $^1$H-NMR (DMSO, 400 MHz), δ (ppm): 3.84 (3H, s, $CH_3$) 3.90 (6H, s, 2×$CH_3$), 4.33-4.50 (4H, m, 2×CH and $CH_2$), 5.91 (1H, d, J=7.00 Hz, OH), 5.97 (1H, d, J=7.00 Hz, OH), 7.45 (2H, d, J=8.12 Hz, ArH), 7.90 (2H, d, J=8.12 Hz, ArH), 8.19 (1H, s, ArH), 8.50 (1H, t, J=6.16 Hz, CONH), 8.45 (2H, d, J=1.12 Hz, ArH), 10.28 (1H, s, CONH); HREI-MS Calcd. for $C_{23}H_{24}N_2O_{10}$: 488.1431. found: 488.1449.

Example 32

Determination of BACE1-Inhibiting Activity

A sodium acetate analytical buffer solution (50 nM, pH 4.5) containing BACE1 (1.0 U/ml), a substrate of BACE1 (750 nM Rh-EVNLDAEFK-Quencher), a compound of the present invention (100 μM) was incubated at 25° C. for 60 minutes. The fluorescence intensity was determined by using a TECANGENios fluorimeter with a slit width of 10 nm, an excitation wavelength of 535 nm and an emission wavelength of 585 nm.

Inhibitory rate(%)={1−[($S$−$S_0$)/($C$−$C_0$)]}*100%

C: the fluorescence intensity of the control (BACE1, substrate and analytical buffer solution) as determined after incubating for 60 minutes.

$C_0$: the fluorescence intensity of the control (BACE1, substrate and analytical buffer solution) as determined after incubating for 0 minute.

S: the fluorescence intensity of the sample (BACE1, substrate, compound of the present invention and analytical buffer solution) as determined after incubating for 60 minutes.

$S_0$: the fluorescence intensity of the sample (BACE1, substrate, compound of the present invention and analytical buffer solution) as determined after incubating for 0 minute.

The results of BACE1-inhibiting activity were shown in Table 1.

TABLE 1

Results of BACE1-inhibiting activity

| Example No. | Concentration of the compound (μM) | Inhibitory rate (%) |
|---|---|---|
| 3 | 100 | 39.0 |
| 14 | 100 | 22.5 |
| 16 | 100 | 26.5 |
| 17 | 100 | 45.3 |
| 18 | 100 | 22.3 |
| 19 | 100 | 35.0 |

The invention claimed is:

1. A compound of formula I, or, prodrugs, pharmaceutically acceptable salts, solvates or hydrates thereof:

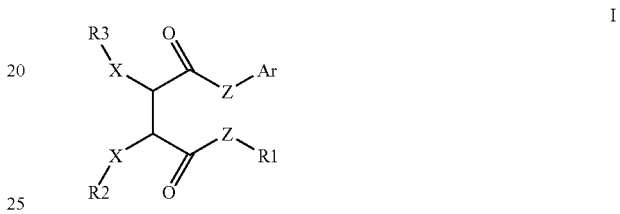

wherein:

X is O, S;

Z is $CH_2$, O, S, NH;

R1 is $C_1$-$C_{22}$ linear or branched alkyl, $C_2$-$C_{22}$ linear or branched alkenyl, $C_3$-$C_8$ cycloalkyl, $C_5$-$C_7$ cycloalkenyl or $Ar_1$, wherein the alkyl or alkenyl radical is unsubstituted or substituted by one or more of the following groups: halogen, nitro, hydroxy, amino, cyano, carboxy, $Ar_2$, $C_3$-$C_8$ cycloalkyl, $C_5$-$C_7$ cycloalkenyl, O—($C_1$-$C_4$)-alkyl or $Ar_2$, CO—($C_1$-$C_4$)-alkyl or $Ar_2$, SO—($C_1$-$C_4$)-alkyl or $Ar_2$, N—[($C_1$-$C_6$)-alkyl]$_2$, NH—($C_1$-$C_6$)-alkyl or $Ar_2$, N—[($C_1$-$C_6$)-alkyl $Ar_2$], COO—($C_1$-$C_6$)-alkyl or $Ar_2$, CONH—($C_1$-$C_6$)-alkyl or $Ar_2$, SONH—($C_1$-$C_6$)-alkyl or $Ar_2$; in addition, the C atoms in the alkyl and alkenyl radicals are optionally spaced by —O—, —S—, —NH—, —N=, —S—, —$Ar_2$—, —SO—, —CO—, —COO—, —CONH—, —SOO—, —SONH—, —N[($C_1$-$C_6$)-alkyl or $Ar_2$]—;

R2 and R3, which are the same or different, are independently selected from the group consisting of hydrogen, hydroxy, $C_1$-$C_{12}$ linear or branched alkyl, $C_2$-$C_{12}$ linear or branched alkenyl, $C_3$-$C_7$ cycloalkyl, $Ar_1$, ($C_1$-$C_6$)—$Ar_1$, —CO—($C_1$-$C_6$)-alkyl or alkenyl or $Ar_1$, —SO—($C_1$-$C_6$)-alkyl or alkenyl or $Ar_1$, SOO—($C_1$-$C_6$)-alkyl or alkenyl;

Ar, $Ar_1$ and $Ar_2$ are independently selected from the group consisting of aromatic carbocycles or heterocycles, wherein each of the cycles consists of 5 to 7 members, and the number of the cycles is monocycle, bicycle or tricycle; the heterocycle includes 1 to 6 heteroatoms selected from the group consisting of O, S, N; the aromatic carbocycles or heterocycles are unsubstituted, or substituted by 1 to 4 groups selected from the group consisting of halogen, nitro, hydroxy, amino, cyano, carboxy, methylol, trifluoromethyl, phenoxy, benzyloxy, anilino, benzylamino, $C_1$-$C_7$ linear or branched alkyl, $C_2$-$C_7$ linear or branched alkenyl, $C_3$-$C_7$ cycloalkyl, $C_5$-$C_7$ cycloalkenyl, —O—($C_1$-$C_6$)-alkyl or alkenyl, —CO—($C_1$-$C_6$)-alkyl or alkenyl, —SO—($C_1$-$C_6$)-alkyl or alkenyl, —NH—($C_1$-$C_6$)-alkyl or alkenyl, —N—[($C_1$-$C_6$)-alkyl or alkenyl]$_2$, —COO—($C_1$-$C_6$)- alkyl or alkenyl, —CONH—($C_1$-$C_6$)-alkyl or alkenyl, —SONH—($C_1$-$C_6$)-alkyl or alkenyl, —CON[($C_1$-$C_6$)-alkyl or alkenyl]$_2$, —SON[($C_1$-$C_6$)-alkyl or alkenyl]$_2$;

the substituent R2X— and the substituent R3X— have the same or different configuration, being R-configuration or S-configuration;

wherein the compound of formula I is selected from the group consisting of:

(1) Methyl L-(2R,3R)-2-[2,3-diacetoxy-3-(naphthalen-2-ylcarbamoyl)-propionylamino]-3-phenyl-propionate;
(2) Methyl L-(2R,3R)-4-{[2,3-diacetoxy-3-(4-phenoxy-phenylcarbamoyl)-propionylamino]methyl}-benzoate;
(3) Methyl L-(2R,3R)-4-[2,3-diacetoxy-3-(4-phenoxy-phenylcarbamoyl)-propionylamino]-butyrate;
(4) Methyl L-(2R,3R)-4-{[3-(3-di-n-propylaminoformyl-phenylcarbamoyl)-2,3-diacetoxy-propionylamino]methyl}-benzoate;
(5) Dimethyl L-(2R,3R)-5-[2,3-diacetoxy-3-(1-methoxycarbonyl-2-phenyl-ethylcarbamoyl)-propionylamino]-isophthalate;
(6) Dimethyl L-(2R,3R)-5-[2,3-diacetoxy-3-(4-methoxycarbonyl-benzylcarbamoyl)-propionylamino]-isophthalate;
(7) L-(2R,3R)—N-benzyl-2,3-diacetoxy-3-(4-benzyl-piperazin-1-yl-formyl)-propionamide;
(8) Methyl L-(2R,3R)-2-(3-benzylcarbamoyl-2,3-dihydroxy-propionylamino)-3-phenyl-propionate;
(9) Methyl L-(2R,3R)-4-[(3-benzylcarbamoyl-2,3-dihydroxy-propionylamino)methyl]-benzoate;
(10) L-(2R,3R)-2-(3-benzylcarbamoyl-2,3-dihydroxy-propionylamino)-3-phenyl-propionic acid;
(11) Methyl L-(2R,3R)-4-(3-benzylcarbamoyl-2,3-dihydroxy-propionylaminomethyl)-cyclohexanecarboxylate;
(12) L-(2R,3R)-4-[(3-benzylcarbamoyl-2,3-dihydroxy-propionylamino)methyl]-benzoic acid;
(13) Methyl L-(2R,3R)-4-(3-benzylcarbamoyl-2,3-dihydroxy-propionylamino)-butyrate;
(14) L-(2R,3R)-4-(3-benzylcarbamoyl-2,3-dihydroxy-propionylamino)-butyric acid;
(15) L-(2R,3R)-4-[(3-benzylcarbamoyl-2,3-dihydroxy-propionylamino)methyl]-cyclohexanecarboxylic acid;
(16) Dimethyl L-(2R,3R)-5-(3-benzylcarbamoyl-2,3-dihydroxy-propionylamino)-isophthalate;
(17) Methyl L-(2R,3R)-4-{[2,3-dihydroxy-3-(naphthalen-2-ylcarbamoyl)-propionylamino]methyl}-benzoate;
(18) Methyl L-(2R,3R)-4-{[2,3-dihydroxy-3-(naphthalen-2-ylcarbamoyl)-propionylamino]methyl}-cyclohexanecarboxylate;
(19) Methyl L-(2R,3R)-2-[2,3-dihydroxy-3-(naphthalen-2-ylcarbamoyl)-propionylamino]-3-phenyl-propionate;
(20) Ethyl L-(2R,3R)-2-[2,3-dihydroxy-3-(4-phenoxy-phenylcarbamoyl)-propionylamino]-3-phenyl-propionate;
(21) Methyl L-(2R,3R)-4-{[2,3-dihydroxy-3-(4-phenoxy-phenylcarbamoyl)-propionylamino]-methyl}-benzoate;
(22) Methyl L-(2R,3R)-4-[2,3-dihydroxy-3-(4-phenoxy-phenylcarbamoyl)-propionylamino]-butyrate;
(23) Methyl L-(2R,3R)-4-[2,3-dihydroxy-3-(naphthalen-2-ylcarbamoyl)-propionylamino]-butyrate;
(24) Ethyl L-(2R,3R)-2-[3-(3-di-n-propylaminoformyl-phenylcarbamoyl)-2,3-dihydroxy-propionylamino]-3-phenyl-propionate;
(25) Benzyl L-(2R,3R)-4-(3-benzylcarbamoyl-2,3-dihydroxy-propionylamino)-butyrate;
(26) Ethyl L-(2R,3R)-4-[2,3-dihydroxy-3-(4-phenoxy-phenylcarbamoyl)-propionylamino]-cyclohexanecarboxylate;
(27) Dimethyl L-(2R,3R)-5-[2,3-dihydroxy-3-(1-methoxycarbonyl-2-phenyl-ethylcarbamoyl)-propionylamino]-isophthalate;
(28) Methyl L-(2R,3R)-4-{[3-(3-di-n-propylaminoformyl-phenylcarbamoyl)-2,3-dihydroxy-propionylamino]methyl}benzoate;
(29) L-(2R,3R)-4-[4-(3-chlorophenyl)-piperazin-1-yl]-2,3-dihydroxy-N-naphthalen-2-yl-4-oxo-butyramide;
(30) L-(2R,3R)-3-{4-[4-(3-chlorophenyl)-piperazin-1-yl]-2,3-dihydroxy-4-oxo-butyrylamino}-N,N-di-n-propyl-benzamide; and
(31) Dimethyl L-(2R,3R)-5-[2,3-dihydroxy-3-(4-methoxycarbonyl-benzylcarbamoyl)-propionylamino]-isophthalate.

2. A process for preparing a compound of formula I according to claim 1, a) as for the compound of formula Ia wherein R2 and R3 both are —CO—$CH_3$, and R1, Ar and Z are as defined in claim 1, the process comprises the steps of:

(i) under the catalysis of an acid such as sulfuric acid, compound 1 (L- or D-tartaric acid) and a lower fatty acid anhydride such as acetic anhydride are reacted by reflux, to obtain compound 2;

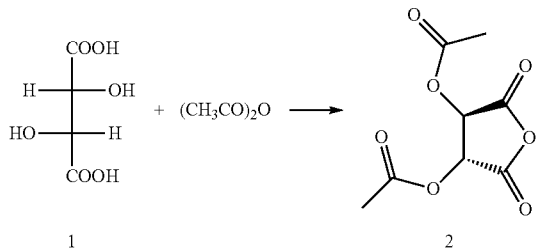

(ii) compound 2 is dissolved in a suitable solvent such as THF, dichloromethane or N,N-dimethylformamide, and acylated with equimolar of ArNH$_2$, to obtain compound 3, wherein Ar is as defined in claim 1;

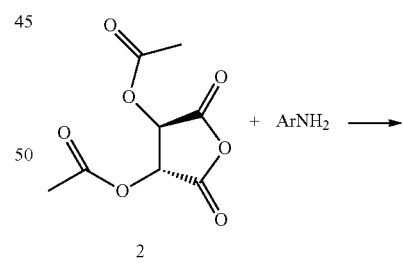

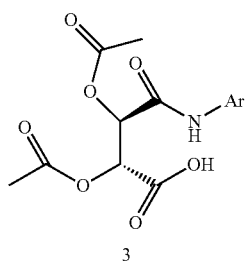

(iii) compound 3 is dissolved in a suitable solvent such as THF, dichloromethane or N,N-dimethylformamide, and, under the catalysis of a suitable amount of dicyclohexylcarbodiimide, camphorsulfonic acid and 4-dimethylaminopyridine, is acylated or esterified with R1ZH (alcohol or amine), wherein R1 and Z are as defined in claim 1, to obtain a specific compound of formula Ia of the invention;

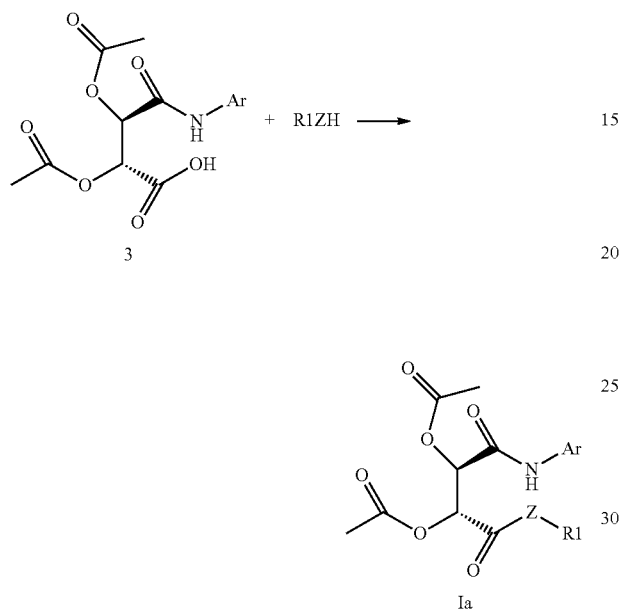

(iv) compound Ia is dissolved in a suitable solvent such as THF, methanol, ethanol, aminolyzed with a concentrated ammonia water or ammonia, hydrolyzed with sodium hydroxide, potassium hydroxide or potassium carbonate, and transesterified with sodium methoxide or sodium ethoxide, to obtain a further specific compound of formula Ia, i.e., a compound of formula Ib, of the invention;

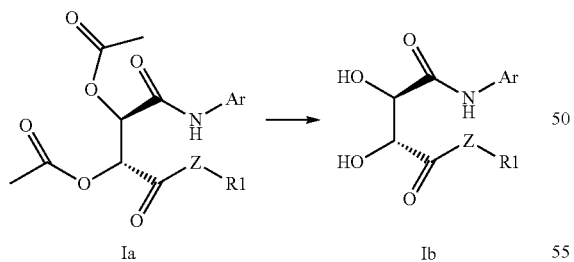

or, b) as for the compound of formula Ib, wherein R1, Ar and Z are as defined in claim 1, the process comprises the steps of:

(i) under the catalysis of an acid such as sulfuric acid, a strong acid type ion exchange resin, compound 1 (L- or D-tartaric acid) is reacted by reflux with a fatty alcohol ROH wherein R is $C_1$-$C_4$ alkyl, such as methanol or ethanol, to obtain compound 2;

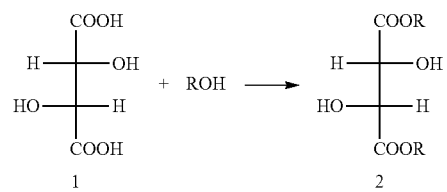

(ii) under the catalysis of a protic acid or Lewis acid such as toluene-p-sulfonic acid or boron trifluoride, compound 2 is reacted by reflux with a ketone of formula R3C(O)R4 wherein R3 and R4 are $C_1$-$C_4$ alkyl, such as acetone, in an inert solvent such as THF or toluene, to obtain a ketal compound 3;

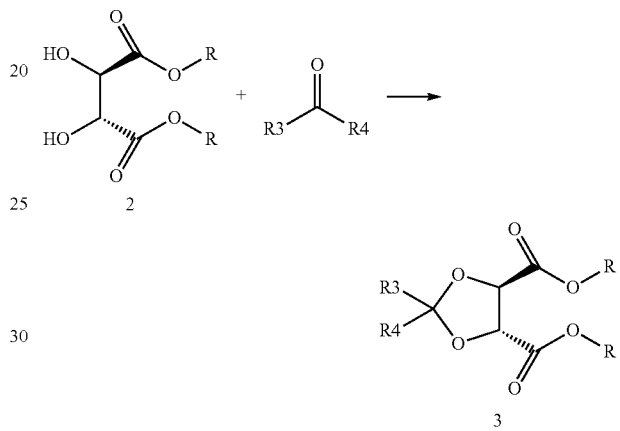

(iii) compound 3 is dissolved in an organic solvent such as THF or dioxane, and is reacted with an aqueous solution of a base such as sodium hydroxide or potassium hydroxide (having a concentration of 1N, and used in a molar ratio of 1:1 in relative to compound 3) at 0° C. to room temperature, and then acidified with an inorganic acid such as hydrochloric acid (having a concentration of 1N), and further extracted with an organic solvent such as dichloromethane, diethyl ether or ethyl acetate, to obtain compound 4;

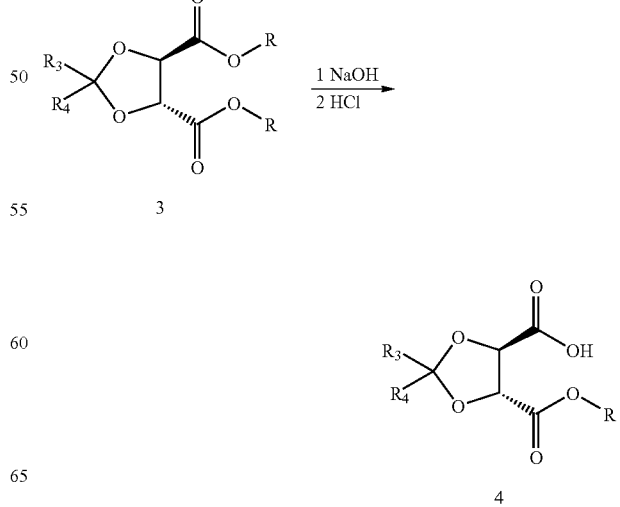

(iv) compound 4 is dissolved in a suitable solvent such as THF, dichloromethane or N,N-dimethylformamide, and, under the catalysis of a suitable amount of dicyclohexylcarbodiimide, camphorsulfonic acid and 4-dimethylaminopyridine, is acylated with ArNH$_2$, to obtain compound 5;

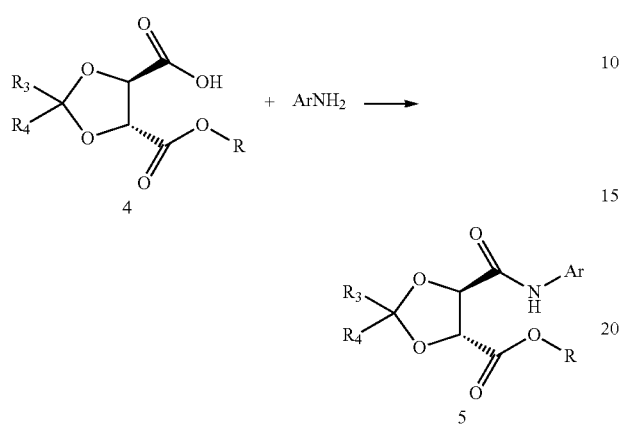

(v) compound 5 is dissolved in an organic solvent such as THF or dioxane, and is reacted with an aqueous solution of a base such as sodium hydroxide or potassium hydroxide (having a concentration of 1N, and used in a molar ratio of 1:1 in relative to compound 5) at 0° C. to room temperature, and then acidified with an inorganic acid such as hydrochloric acid (having a concentration of 1N), and further extracted with an organic solvent such as dichloromethane, diethyl ether or ethyl acetate, to obtain compound 6;

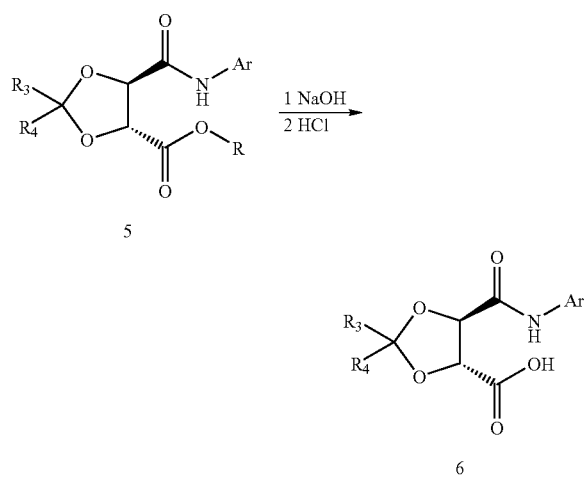

(vi) compound 6 is dissolved in a suitable solvent such as THF, dichloromethane or N,N-dimethylformamide, and, under the catalysis of a suitable amount of dicyclohexylcarbodiimide, camphorsulfonic acid and 4-dimethylaminopyridine, is esterified or acylated with R1ZH (alcohol or amine), wherein R1 and Z are as defined above, to obtain compound 7;

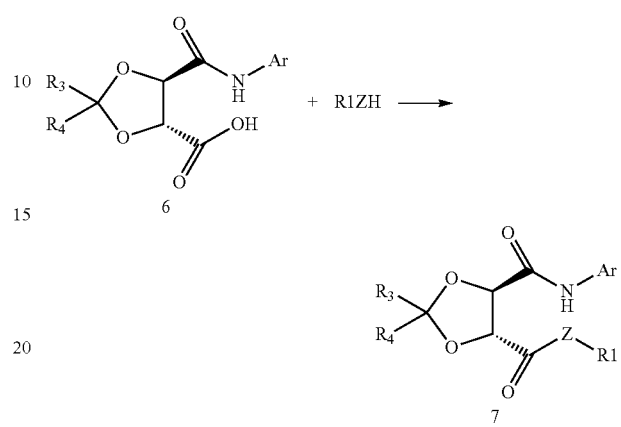

(vii) compound 7 is dissolved in a suitable solvent such as methanol or ethanol, and, under the catalysis of a suitable amount of a protic acid such as hydrochloric acid or sulfuric acid, is deprotected to remove acetonide group, to obtain a specific compound of formula Ib of the invention,

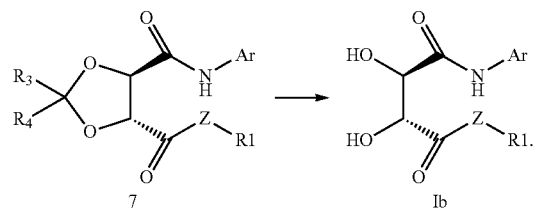

3. A pharmaceutical composition comprising a compound of formula I according to claim 1, or, prodrugs, pharmaceutically acceptable salts, solvates or hydrates thereof, and at least one pharmaceutically acceptable carrier or excipient.

4. A method of treating diseases induced by aggregation or deposition of β-amyloid peptide comprising administering to a patient in need thereof the compound according to claim 1 or prodrugs, pharmaceutically acceptable salts, solvates or hydrates thereof.

5. The method according to claim 4, wherein the relevant diseases induced by aggregation or deposition of β-amyloid peptide are selected from the group consisting of Alzheimer's disease, amyloid degenerative angiopathy, Kuru's diseases and Down's syndrome.

* * * * *